United States Patent
Badylak et al.

(10) Patent No.: US 11,638,724 B2
(45) Date of Patent: May 2, 2023

(54) OCULAR APPLICATIONS OF MATRIX BOUND VESICLES (MBVS)

(71) Applicant: University of Pittsburgh—Of the Commonwealth System of Higher Education, Pittsburgh, PA (US)

(72) Inventors: Stephen F. Badylak, West Lafayette, IN (US); Anne E. Faust, Pittsburgh, PA (US); George S. Hussey, Cranberry Township, PA (US); Yolandi Van der Merwe, Pittsburgh, PA (US); Michael Brandt Steketee, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 532 days.

(21) Appl. No.: 16/610,866

(22) PCT Filed: May 4, 2018

(86) PCT No.: PCT/US2018/031190
§ 371 (c)(1),
(2) Date: Nov. 4, 2019

(87) PCT Pub. No.: WO2018/204848
PCT Pub. Date: Nov. 8, 2018

(65) Prior Publication Data
US 2021/0137988 A1  May 13, 2021

Related U.S. Application Data

(60) Provisional application No. 62/502,271, filed on May 5, 2017.

(51) Int. Cl.
| | |
|---|---|
| *A61K 35/22* | (2015.01) |
| *A61K 9/00* | (2006.01) |
| *A61K 38/44* | (2006.01) |
| *A61K 45/06* | (2006.01) |
| *A61K 9/51* | (2006.01) |
| *C12N 15/113* | (2010.01) |
| *A61P 27/02* | (2006.01) |
| *A61P 27/06* | (2006.01) |
| *A61K 9/06* | (2006.01) |

(52) U.S. Cl.
CPC ............ *A61K 35/22* (2013.01); *A61K 9/0048* (2013.01); *A61K 9/06* (2013.01); *A61K 9/5176* (2013.01); *A61K 38/44* (2013.01); *A61K 45/06* (2013.01); *A61P 27/02* (2018.01); *A61P 27/06* (2018.01); *C12N 15/1135* (2013.01); *C12Y 104/03013* (2013.01); *C12N 2310/141* (2013.01)

(58) Field of Classification Search
CPC .... A61K 35/22; A61K 9/0048; A61K 9/5176; A61K 38/44; A61K 45/06; A61P 27/02; A61P 27/06; C12N 15/1135; C12N 2310/141; C12Y 104/03013
See application file for complete search history.

(56) References Cited

U.S. PATENT DOCUMENTS

| | | |
|---|---|---|
| 4,902,508 A | 2/1990 | Badylak et al. |
| 4,956,178 A | 9/1990 | Badylak et al. |
| 4,978,668 A | 12/1990 | Babbs et al. |
| 5,007,927 A | 4/1991 | Badylak et al. |
| 5,281,422 A | 1/1994 | Badylak et al. |
| 5,352,463 A | 10/1994 | Badylak et al. |
| 5,354,274 A | 12/1994 | Badylak et al. |
| 5,372,821 A | 12/1994 | Badylak et al. |
| 5,443,505 A | 8/1995 | Wong et al. |
| 5,554,389 A | 9/1996 | Badylak et al. |
| 5,573,784 A | 11/1996 | Badylak et al. |
| 5,645,860 A | 7/1997 | Knapp et al. |
| 5,711,969 A | 1/1998 | Umesh et al. |
| 5,753,267 A | 5/1998 | Badylak et al. |
| 5,762,966 A | 6/1998 | Knapp et al. |
| 5,766,242 A | 6/1998 | Wong et al. |
| 5,866,414 A | 2/1999 | Badylak et al. |
| 5,869,079 A | 2/1999 | Wong et al. |
| 5,955,110 A | 9/1999 | Patel et al. |
| 5,997,575 A | 12/1999 | Whitson et al. |
| 6,096,347 A | 8/2000 | Geddes et al. |
| 6,099,567 A | 8/2000 | Badylak et al. |

(Continued)

FOREIGN PATENT DOCUMENTS

| | | |
|---|---|---|
| WO | WO 96/31225 A1 | 10/1996 |
| WO | WO 00/32209 A2 | 6/2000 |

(Continued)

OTHER PUBLICATIONS

Kim DK, Nishida H, An SY, Shetty AK, Bartosh TJ, Prockop DJ. Chromatographically isolated CD63+CD81+ extracellular vesicles from mesenchymal stromal cells rescue cognitive impairments after TBI. Proc Natl Acad Sci U S A. Jan. 5, 2016;113(1):170-5. doi: 10.1073/pnas.1522297113. Epub Dec. 22, 2015. PMID: 26699510; PMCID.*

(Continued)

*Primary Examiner* — Kade Ariani
(74) *Attorney, Agent, or Firm* — Klarquist Sparkman, LLP

(57) ABSTRACT

Methods are disclosed herein for increasing retinal ganglion cell survival in a subject in need thereof. These methods include selecting a subject in need of increased retinal ganglion cell survival and administering a therapeutically effective amount of isolated nanovesicles derived from an extracellular matrix (MBVs) to the subject.

17 Claims, 14 Drawing Sheets

Specification includes a Sequence Listing.

(56) References Cited

U.S. PATENT DOCUMENTS

| | | |
|---|---|---|
| 6,126,686 A | 10/2000 | Badylak et al. |
| 6,187,039 B1 | 2/2001 | Hiles et al. |
| 6,241,981 B1 | 6/2001 | Cobb et al. |
| 6,251,090 B1 | 6/2001 | Avery et al. |
| 6,299,895 B1 | 10/2001 | Hammang et al. |
| 6,331,319 B1 | 12/2001 | Badylak et al. |
| 6,375,989 B1 | 4/2002 | Badylak et al. |
| 6,413,540 B1 | 7/2002 | Yaacobi |
| 6,416,777 B1 | 7/2002 | Yaacobi |
| 6,485,723 B1 | 11/2002 | Badylak et al. |
| 6,576,265 B1 | 6/2003 | Spievack |
| 6,579,538 B1 | 6/2003 | Spievack |
| 6,696,270 B2 | 2/2004 | Badylak et al. |
| 6,699,493 B2 | 3/2004 | Wong et al. |
| 6,783,776 B2 | 8/2004 | Spievack |
| 6,793,939 B2 | 9/2004 | Badylak |
| 6,849,273 B2 | 2/2005 | Spievack |
| 6,852,339 B2 | 2/2005 | Spievack |
| 6,861,074 B2 | 3/2005 | Spievack |
| 6,887,495 B2 | 5/2005 | Spievack |
| 6,890,562 B2 | 5/2005 | Spievack |
| 6,890,563 B2 | 5/2005 | Spievack |
| 6,890,564 B2 | 5/2005 | Spievack |
| 6,893,666 B2 | 5/2005 | Spievack |
| 6,918,396 B1 | 7/2005 | Badylak et al. |
| 7,776,596 B2 | 8/2010 | Badylak |
| 7,815,686 B2 | 10/2010 | Badylak |
| 7,820,634 B2 | 10/2010 | Badylak et al. |
| 7,919,121 B2 | 4/2011 | Badylak et al. |
| 8,003,131 B2 | 8/2011 | Badylak |
| 8,029,774 B2 | 10/2011 | Beckman et al. |
| 8,084,048 B2 | 12/2011 | Badylak |
| 8,409,625 B2 | 4/2013 | Badylak |
| 8,535,719 B2 | 9/2013 | Badylak et al. |
| 8,647,677 B2 | 2/2014 | Badylak |
| 9,277,999 B2 | 3/2016 | Badylak et al. |
| 9,340,602 B2 | 5/2016 | Agrawal et al. |
| 9,480,776 B2 | 11/2016 | Badylak et al. |
| 9,848,987 B2 | 12/2017 | Badylak et al. |
| 9,861,662 B2 | 1/2018 | Badylak |
| 10,092,676 B2 | 10/2018 | Amoroso et al. |
| 10,286,119 B2 | 5/2019 | Badylak et al. |
| 10,729,813 B2 | 8/2020 | Badylak et al. |
| 11,291,688 B2 | 4/2022 | Badylak et al. |
| 11,389,566 B2 | 7/2022 | Ramer et al. |
| 11,389,569 B2 | 7/2022 | Badylak et al. |
| 11,406,736 B2 | 8/2022 | Badylak et al. |
| 11,413,375 B2 | 8/2022 | Badylak et al. |
| 2004/0078076 A1 | 4/2004 | Badylak et al. |
| 2004/0187877 A1 | 9/2004 | Badylak et al. |
| 2004/0191226 A1 | 9/2004 | Badylak |
| 2006/0292227 A1 | 12/2006 | McPherson |
| 2007/0135906 A1 | 6/2007 | Badylak et al. |
| 2009/0053279 A1 | 2/2009 | Badylak et al. |
| 2010/0297212 A1 | 11/2010 | Badylak |
| 2011/0097378 A1 | 4/2011 | Badylak |
| 2011/0165126 A1 | 7/2011 | Badylak et al. |
| 2011/0184439 A1 | 7/2011 | William et al. |
| 2014/0031256 A1 | 1/2014 | Lim |
| 2014/0356331 A1 | 12/2014 | Badylak et al. |
| 2018/0125897 A1 | 5/2018 | Badylak et al. |
| 2018/0200405 A1 | 7/2018 | Badylak et al. |
| 2018/0243473 A1 | 8/2018 | Badylak et al. |
| 2020/0261624 A1 | 8/2020 | Crapo et al. |
| 2020/0360565 A1 | 11/2020 | Badylak et al. |
| 2021/0008251 A1 | 1/2021 | Badylak et al. |
| 2021/0106526 A1 | 4/2021 | Badylak et al. |
| 2021/0137988 A1 | 5/2021 | Badylak et al. |
| 2021/0244396 A1 | 8/2021 | Badylak et al. |
| 2021/0244855 A1 | 8/2021 | Badylak et al. |
| 2021/0260246 A1 | 8/2021 | Badylak et al. |
| 2021/0268148 A1 | 9/2021 | Badylak et al. |
| 2022/0143265 A1 | 5/2022 | Badylak et al. |
| 2022/0249549 A1 | 8/2022 | Badylak et al. |

FOREIGN PATENT DOCUMENTS

| | | |
|---|---|---|
| WO | WO 00/40089 A1 | 7/2000 |
| WO | WO 01/28474 A1 | 4/2001 |
| WO | WO 02/089767 A1 | 11/2002 |
| WO | WO 03/059221 A1 | 7/2003 |
| WO | WO 03/059284 A2 | 7/2003 |
| WO | WO 2005/079844 A2 | 9/2005 |
| WO | WO 2010/099463 A2 | 9/2010 |
| WO | WO 2015/179227 A1 | 11/2015 |
| WO | WO 2017/151862 A1 | 9/2017 |
| WO | WO 2018/161028 A1 | 9/2018 |
| WO | WO 2018/161034 A1 | 9/2018 |
| WO | WO 2018/204848 A1 | 11/2018 |
| WO | WO 2019/213482 A1 | 11/2019 |
| WO | WO 2021/081231 A1 | 4/2021 |
| WO | WO 2021/211885 A1 | 10/2021 |
| WO | WO 2021/217018 A1 | 10/2021 |
| WO | WO 2022/055559 A1 | 3/2022 |

OTHER PUBLICATIONS

Faust et al., "Urinary bladder extracellular matrix hydrogels and matrix-bound vesicles differentially regulate central nervous system neuron viability and axon growth and branching," *Journal of Biomaterials Applications* 31(9): 1277-1295 (E-pub Mar. 9, 2017) (Abstract only).

Huleihel et al., "Matrix-bound nanovesicles within ECM bioscaffolds," *Science Advances* 2: e1600502, pp. 1-11 (Jun. 10, 2016).

International Search Report and Written Opinion from parent PCT Application No. PCT/US2018/031190, 10 pages (dated Jul. 25, 2018).

Ren et al., "Developing extracellular matrix technology to treat retinal or optic nerve injury," *eNeuro* 2(5): e0077-15, pp. 1-14 (Sep. 18, 2015).

Van der Merwe et al., "Matrix bound vesicles and miRNA cargoes are bioactive factors within extracellular matrix bioscaffolds," *Neural Regeneration Research* 12(10): 1597-1599 (Oct. 2017).

Alarcon-Martinez et al., "Short and long term axotomy-induced ERG changes in albino and pigmented rats," Molecular Vision 15: 2373-2383, 2009.

Alberts et al., "Fractionation of cells," Molecular Biology of the Cell. 4th edition. Garland Science, 2002.

Ali et al., "Isolation and Characterization of Calcifying Matrix Vesicles from Epiphyseal Cartilage," Proceedings of the National Academy of Sciences 67.3: 1513-1520, Nov. 1970.

Ali, "Analysis of matrix vesicles and their role in the calcification of epiphyseal cartilage," Federation Proceedings 35.2: 135-142, 1976.

Ali, "Matrix vesicles and apatite nodules in arthritic cartilage," *Perspectives in inflammation*, Springer, Dordrecht: 211-223, 1977.

Alicuben and Demeester, "Onlay ventral hernia repairs using porcine non-cross-linked dermal biologic mesh," Hernia 18: 705-712, 2014.

Ambati et al., "Transscleral Delivery of Bioactive Protein to the Choroid and Retina," Ophthalmology & Visual Science 41.5: 1186-1191, Apr. 2000.

Anderson, "Vesicles Associated with Calcification in the Matrix of Epiphyseal Cartilage," The Journal of Cell Biology 41: 59-72, 1969.

Anderson, "Molecular biology of matrix vesicles," Clinical Orthopaedics and Related Research 314: 266-280, 1995.

Anderson, "Matrix vesicles and calcification," Current Rheumatology Reports 5.3: 222-226, 2003.

Bab et al., "Ultrastructural and biochemical study of extracellular matrix vesicles in normal alveolar bone of rats," Cell and Tissue Research 202.1: 1-7, 1979.

Badylak et al., "Esophageal Preservation in Five Male Patients After Endoscopic Inner-Layer Circumferential Resection in the Setting of Superficial Cancer: A Regenerative Medicine Approach with Biologic Scaffold," Tissue Engineering: Part A 17.11 and 12: 1643-1650, 2011.

(56) References Cited

OTHER PUBLICATIONS

Badylak, "Decellularized allogeneic and xenogeneic tissue as a bioscaffold for regenerative medicine: factors that influence the host response," Annals of Biomedical Engineering 42.7: 1517-1527, 2014.
Badylak et al., "Reprint of: Extracellular matrix as a biological scaffold material: Structure and function," Acta Biomaterialia 23: S17-S26, 2015.
Barres et al., "Immunological, Morphological, and Electrophysiological Variation among Retinal Ganglion Cells Purified by Panning," Neuron 1: 791-803, Nov. 1988.
Bejjani et al., "Safety and efficacy of the porcine small intestinal submucosa dural substitute: results of a prospective multicenter study and literature review," J Neurosurg. 106: 1028-1033, 2007.
Ben-Dov et al., "Cell and Microvesicle Urine microRNA Deep Sequencing Profiles from Healthy Individuals: Observations with Potential Impact on Biomarker Studies," PLoS One 11.1: e0147249, 2016 (10 pages).
Bobrie et al., "Exosome Secretion: Molecular Mechanisms and Roles in Immune Responses," Traffic 12: 1659-1668, 2011.
Burzyn et al., "A Special Population of Regulatory T Cells Potentiates Muscle Repair," Cell 155.6: 1282-1295, Dec. 2013.
Chen et al., "Optic Neuropathy Due to Microbead-Induced Elevated Intraocular Pressure in the Mouse," Investigative Ophthalmology & Visual Science 52.1: 36-44, Jan. 2011.
Cortiella et al., "Influence of Acellular Natural Lung Matrix on Murine Embryonic Stem Cell Differentiation and Tissue Formation," Tissue Engineering: Part A 16.8: 2565-2580, 2010.
Crapo et al., "An overview of tissue and whole organ decellularization process," Biomaterials 32: 3233-3243, 2011.
Darlington et al., "Innate Immune-Mediated Neuronal Injury Consequent to Loss of Astrocytes," J Neuropathol Exp Neurol. 67.6: 590-599, Jun. 2008.
De Jong et al., "Extracellular vesicles: potential roles in regenerative medicine," Frontiers in Immunology 5:608: 1-13, Dec. 2014.
Deatherage and Cookson, "Membrane Vesicle Release in Bacteria, Eukaryotes, and Archaea: a Conserved yet Underappreciated Aspect of Microbial Life," Infection and Immunity 80.6: 1948-1957, Jun. 2012.
Deutsch et al., "Purification and further characterization of isolated matrix vesicles from rat alveolar bone," Metabolic Bone Disease and Related Research 3.3: 209-214, 1981.
Dziki et al., "Extracellular Matrix Bioscaffolds as Immunomodulatory Biomaterials," Tissue Engineering: Part A 23: 19 and 20: 1152-1159, 2017.
Escola et al., "Selective Enrichment of Tetraspan Proteins on the Internal Vesicles of Multivesicular Endosomes and on Exosomes Secreted by Human B-lymphocytes," The Journal of Biological Chemistry, 273.32: 20121-20127, 1998.
Faust et al., "Urinary bladder extracellular matrix hydrogels and matrix-bound vesicles differentially regulate central nervous system neuron viability and axon growth and branching," Journal of Biomaterials Applications 31.9: 1277-1295, 2017.
Freytes et al., "Preparation and rheological characterization of a gel form of the porcine urinary bladder matrix," Biomaterials 29: 1630-1637, 2008.
Gibson et al. "Tissue extracellular matrix nanoparticle presentation in electrospun nanofibers," BioMed Research International 2014: 469120, 2014.
Gilbert et al., "Production and characterization of ECM power: implications for tissue engineering applications," Biomaterials 26: 1431-1435, 2005.
Gohr et al., "Calcific Tendonitis : A Model," Connective Tissue Research 48.6: 286-291, May 2007.
Goldberg et al., "Retinal Ganglion Cells Do No Extend Axons by Default: Promotion by Neurotrophic Signaling and Electrical Activity," Neuron 33: 689-702, Feb. 2002.
Greening et al., "Exosomes and their roles in immune regulation and cancer," Seminars in Cell & Developmental Biology 40: 72-81, 2015.
Greening et al., "A protocol for exosome isolation and characterization: evaluation of ultracentrifugation, density-gradient separation, and immunoaffinity capture methods," Proteomic Profiling. Humana Press, New York, NY, pp. 179-209, 2015.
Hargett and Bauer, "On the origin of microparticles: From "platelet dust" to mediators of intercellular communication," Pulmonary Circulation 3.2: 329-340, 2013.
Hasegawa et al., "Ultrastructural and biochemical aspects of matrix vesicle-mediated mineralization," Japanese Dental Science Review 53: 34-45, 2017.
Hirschman et al., "Neutral Peptidase Activities in Matrix Vesicles from Bovine Fetal Alveolar and Dog Osteosarcoma," Calcified Tissue International 35: 791-797, 1983.
Huang et al., "Characterization of human plasma-derived exosomal RNAs by deep sequencing," BMC Genomics 14: 319 (14 pages), 2013.
Huleihel et al., "Matrix-Bound Nanovesicles Recapitulate Extracellular Matrix Effects on Macrophage Phenotype," Tissue Engineering: Part A 23.21 and 22: 1283-1294, 2017.
Hussey et al. "Il-33 As a Key Signaling Molecule for the Therapeutic Effects of ECM Bioscaffolds for Cardiac Repair," Tissue Engineering Part A 23.Supplement 1: Abstract No. 107, Dec. 2017.
Hussey et al., "Extracellular Matrix Bioscaffolds for Building Gastrointestinal Tissue," Cellular and Molecular Gastroenterology and Hepatology 5.1: 1-13, 2018.
Hussey et al., "Matrix bound nanovesicle-associated IL-33 activates a pro-remodeling macrophage phenotype via a non-canonical, ST2-independent pathway", Journal of Immunology and Regenerative Medicine 3: 26-35, 2019.
Hussey et al., "Lipidomics and RNA sequencing reveal a novel subpopulation of nanovesicle within extracellular matrix biomaterials," Sci Adv. 6:eaay4361, Mar. 2020 (13 pages).
Ji et al., "Deep Sequencing of RNA from Three Different Extracellular Vesicle (EV) Subtypes Released from the Human LIM1863 Colon Cancer Cell Line Uncovers Distinct Mirna-Enrichment Signatures," PLoS One 9.10: e110314, 2014 (15 pages).
Kapustin et al., "Vascular Smooth Muscle Cell Calcification is Mediated by Regulated Exosome Secretion," Circulation Research 116.8: 1312-1323, 2015.
Kim et al., "Chromatographically isolated CD63+CD81+ extracellular vesicles from mesenchymal stromal cells rescue cognitive impairments after TBI," Proc Natl Acad Sci. 113.1: 170-175, Jan. 2016.
Koga et al., "Exosome can prevent RNase from degrading microRNA in feces," Journal of Gastrointestinal Oncology 2.4: 215-222, Dec. 2011.
Konoshenko et al., "Isolation of Extracellular Vesicles: General Methodologies and Latest Trends," BioMed Research International 2018: 8545347, 2018 (27 pages).
Krill, "Extracellular Matrix-Derived Nanoparticles for Imaging and Immunomodulation,": Thesis, Johns Hopkins University, Baltimore, MD, May 2016 (62 pages).
Kuchen et al., "Regulation of microRNA Expression and Abundance during Lymphopoiesis," Immunity 32.6: 828-839, Jun. 2010.
Kuswanto et al., "Poor repair of skeletal muscle in aging mice reflects a defect in local, interleukin-33-dependent, accumulation of regulatory T cells," Immunity 44.2: 355-367, Feb. 2016.
Lamichhane et al., "Emerging Roles for Extracellular Vesicles in Tissue Engineering and Regenerative Medicine," Tissue Engineering: Part B 21.1: 45-54, 2015.
Liddelow et al., "Neurotoxic reactive astrocytes are induced by activated microglia," Nature 541.7638: 481-487, Jan. 2017.
Londono and Badylak, "Biologic Scaffolds for Regenerative Medicine: Mechanisms of In vivo Remodeling," Annals of Biomedical Engineering 43.3: 577-592, Mar. 2015.
Longo et al., "Scaffolds in Tendon Tissue Engineering," Stem Cells International 2012: 517165, 2012 (12 pages).
Mahida et al., "Extracellular Vesicles in ARDS: New Insights into Pathogenesis with Novel Clinical Applications," Annual Update in Intensive Care and Emergency Medicine 2020, Springer Nature Switzerland AG: 53-65, 2020.
Malda et al., "Extracellular vesicles—new tool for joint repair and regeneration," Nat Rev Rheumatol. 12.4: 243-249, Apr. 2016.

(56) References Cited

OTHER PUBLICATIONS

Mansour-Robaey et al., "Effects of ocular injury and administration of brain-derived neurotrophic factor on survival and regrowth of axotomized retinal ganglion cells," Proc Natl Acad Sci USA 91: 1632-1636, Mar. 1994.

Martin et al., "Isolation and purification of extracellular matrix vesicles from blood vessels," Preparative Biochemistry & Biotechnology 22.2: 87-103, 1992.

Mase, Jr. et al. "Clinical application of an acellular biologic scaffold for surgical repair of a large, traumatic quadriceps femoris muscle defect," Orthopedics 33.7: 511, 2010.

McCloy et al., "Partial inhibition of Cdk1 in G2 phase overrides the SAC and decouples mitotic events," Cell Cycle 13.9: 1400-1412, May 2014.

McKeon et al., "Reduction of Neurite Outgrowth in a Model of Glial Scarring following CNS injury Is Correlated with the Expression of Inhibitory Molecules on Reactive Astrocytes," The Journal of Neuroscience 11.11: 3398-3411, Nov. 1991.

McKeon et al., "The Chondroitin Sulfate Proteoglycans Neurocan and Phosphacan Are Expressed by Reactive Astrocytes in the Chronic CNS Glial Scar," The Journal of Neuroscience 19.24: 10778-10788, Dec. 1999.

Medberry et al., "Hydrogels derived from central nervous system extracellular matrix," Biomaterials 34: 1033-1040, 2013.

Miller, "Role of IL-33 in inflammation and disease," Journal of Inflammation 8: 22, 2011 (12 pages).

Mu et al., "Host Matrix Modulation by Tumor Exosomes Promotes Motility and Invasiveness," Neoplasia 15.8: 875-887, Aug. 2013.

Muhlrad et al., "Occurrence of Actin-Like Protein in Extracellular Matrix Vesicles," Calcif Tissue Int. 34: 376-381, 1982.

Narita et al., "Immune responses in patients with esophageal cancer treated with SART1 peptide-pulsed dendritic cell vaccine," International Journal of Oncology 46: 1699-1709, 2015.

Nawaz et al., "The emerging role of extracellular vesicles as biomarkers for urogenital cancers," Nature Reviews Urology 11.12: 688-701, 2014.

Owens and Mutter, "Statistical Brief #112: Emergency department visits related to eye injuries, 2008," Healthcare cost and utilization project (HCUP) statistical briefs, Rockville (MD): Agency for Healthcare Research and Quality (US), 2006. Retrieved Nov. 14, 2022: <https://www.ncbi.nlm.nih.gov/books/NBK56035/?report=classic>.

Panagiotou et al., "Microvesicles as Vehicles for Tissue Regeneration: Changing of the Guards," Curr Pathobiol Rep 4: 181-187, 2016.

Quijano et al., "Matrix-Bound Nanovesicles: The Effects of Isolation Method upon Yield, Purity, and Function," Tissue Engineering: Part C 26.10: 528-540, 2020.

Rosario et al., "Decellularization and sterilization of porcine urinary bladder matrix for tissue engineering in the lower urinary tract," Regen Med. 3.2: 145-156, 2008.

Rutnam et al., "miRNAs regulate expression and function of extracellular matrix molecules," Matrix Bol. 32.2: 74-85, Mar. 2013.

Sabin and Kikyo, "Microvesicles as mediators of tissue regeneration," Translational Research 163.4: 286-295, 2014.

Salzberg, "Nonexpansive Immediate Breast Reconstruction Using Human Acellular Tissue Matrix Graft (AlloDerm)," Ann Plast Surg. 57: 1-5, 2006.

Schurgers et al., "Initiation and Propagation of Vascular Calcification Is Regulated by a Concert of Platelet—and Smooth Muscle Cell-Derived Extracellular Vesicles," Front Cardiovasc Med. 5: 36, 2018 (13 pages).

Sela et al., "Ultrastructural and biochemical characterization of extracellular matrix vesicles in healing alveolar bone sockets: Preliminary indications for the presence of contractile proteins," Metabolic Bone Disease and Related Research 1.3: 185-191, 1978.

Sellaro et al., "Maintenance of Hepatic Sinusoidal Endothelial Cell Phenotype In Vitro Using Organ-Specific Extracellular Matrix Scaffolds," Tissue Engineering 13.9: 2301-2310, 2007.

Shapiro et al., "Matrix Vesicles: Are They Anchored Exosomes?", Bone 79: 29-36, Oct. 2015.

Shaw et al., "Topical administration of a Rock/Net inhibitor promotes retinal ganglion cell survival and axon regeneration after optic nerve injury," Exp Eye Res. 158: 33-42, May 2017.

Sicari et al., "A Murine Model of Volumetric Muscle Loss and a Regenerative Medicine Approach for Tissue Replacement," Tissue Engineering: Part A 18.19 and 20: 1941-1948, 2012.

Stevanato et al., "Investigation of Content, Stoichiometry and Transfer of miRNA from Human Neural Stem Cell Line Derived Exosomes," PLoS One 11.1: e0146353, 2016 (13 pages).

Thery et al., "Molecular Characterization of Dendritic Cell-derived Exosomes: Selective Accumulation of the Heat Shock Protein hsc73," The Journal of Cell Biology 147.3: 599-610, Nov. 1999.

Thery et al., "Proteomic Analysis of Dendritic Cell-Derived Exosomes: A Secreted Subcellular Compartment Distinct from Apoptotic Vesicles," The Journal of Immunology 166.12: 7309-7318, 2001.

Thouverey et al., "Proteomic characterization of biogenesis and functions of matrix vesicles released from mineralizing human osteoblast-like cells," Journal of Proteomics 74: 112-1134, 2011.

Tian et al., "A doxorubicin delivery platform using engineered natural membrane vesicle exosomes for targeted tumor therapy," Biomaterials 35: 2383-2390, 2014.

Tropea et al., "Synergistic Effects of Brain-Derived Neurotrophic Factor and Chondroitinase ABC on Retinal Fiber Sprouting after Denervation of the Superior Colliculus in Adult Rats," The Journal of Neuroscience 23.18: 7034-7044, Aug. 2003.

Turnquist et al., "IL-33 expands suppressive CD11b+ GR-1int and regulatory T cells (Treg), including ST2L+ Foxp3+ cells, and mediates Treg-dependent promotion of cardiac allograft survival," J Immunol. 187.9: 4598-4610, Nov. 2011.

Vaananen and Korhonen, "Matrix Vesicles in Chicken Epiphyseal Cartilage. Separation from Lysosomes and the Distribution of Inorganic Pyrophosphatase Activity," Calcif Tissue Int. 28: 65-72, 1979.

Van der Merwe et al., "An Elastomeric Polymer Matrix, PEUU-Tac, Delivers Bioactive Tacrolimus Transdurally to the CNS in Rat," EBioMedicine 26: 47-59, 2017.

Van der Merwe et al., "Matrix-bound nanovesicles prevent ischemia-induced retinal ganglion cell axon degeneration and death and preserve visual function," Scientific Reports 9: 3482, 2019 (15 pages).

Van der Pol et al., "Classification, Functions, and Clinical Relevance of Extracellular Vesicles," Pharmacological Reviews 64.3: 676-705, 2012.

Wagner and Radisic, "A New Role for Extracellular Vesicles in Cardiac Tissue Engineering and Regenerative Medicine," Adv Nanobiomed Res. 1.11: 2100047, Nov. 2021 (45 pages).

Wang et al., "Comparison of In Vivo Adipogenic Capabilities of Two Different Extracellular Matrix Microparticle Scaffolds," Plastic and reconstructive surgery 131.2: 174e-187e, 2013.

Wolf, "The Nature and Significance of Platelet Products in Human Plasma," Brit J Haemat. 13.3: 269-288, 1967.

Wolf et al., "Immunomodulatory Extracellular Matrix Nanoparticles," Tissue Engineering Part A 21.140: S-52, 2015 (1 page).

Wu et al., "Extracellular vesicles as emerging targets in cancer: recent developments from bench to bedside," Biochim Biophys Acta 1868.2: 538-563, Dec. 2017.

Wuthier et al., "Non-enzymatic isolation of matrix vesicles: characterization and initial studies on 45Ca and 32P-orthophosphate metabolism," Metabolic Bone Disease and Related Research 1.2: 125-136, 1978.

Wynn and Ramalingam, "Mechanisms of fibrosis: therapeutic translation for fibrotic disease," Nat Med 18.7: 1028-1040, 2012.

Yanez-Mo et al., "Biological properties of extracellular vesicles and their physiological functions," Journal of Extracellular Vesicles 4: 27066, 2015 (60 pages).

Zhou et al., "Label-free quantification proteomics reveals novel calcium binding proteins in matrix vesicles isolated from mineralizing Saos-2 cells," BioScience Trends 7.3: 144-151, 2013.

\* cited by examiner

RGC viability

RGC neurite growth

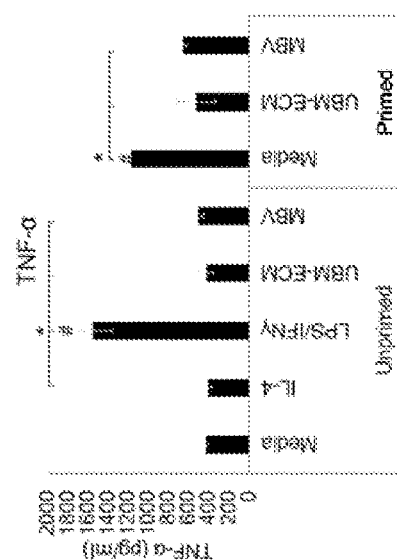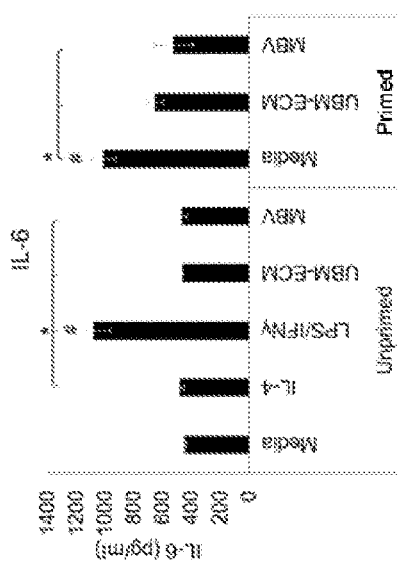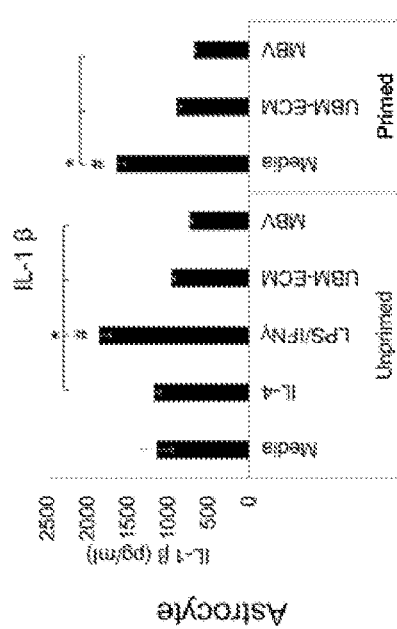

FIG. 2G

| Microglia | Condition | IL-1β (μg/ml) | IL-6 (μg/ml) | TNF-α (μg/ml) |
|---|---|---|---|---|
| Unprimed | Media | 202.4 ± 30.4 | 1314.8 ± 26.7 | 178.2 ± 18.2 |
| | IL-4 | 201.6 ± 12.7 | 1105.5 ± 48.2 | 109.5 ± 5.9 |
| | LPS/IFNγ | 499.6 ± 28.4 | 2283.0 ± 142.9 | 474.5 ± 27.6 |
| | UBM-ECM | 186.4 ± 13.9 | 584.3 ± 76.3 | 169.8 ± 13.5 |
| | MBV | 250.2 ± 16.0 | 1199.4 ± 69.6 | 191.9 ± 16.4 |
| Primed | Media | 502.6 ± 65.1 | 1825.9 ± 120.4 | 524.8 ± 70.8 |
| | UBM-ECM | 171.3 ± 9.6 | 737.2 ± 26.4 | 153.5 ± 13.45 |
| | MBV | 197.2 ± 17.1 | 952.3 ± 24.9 | 150.0 ± 12.7 |

FIG. 2H

| Astrocytes | Condition | IL-1β (μg/ml) | IL-6 (μg/ml) | TNF-α (μg/ml) |
|---|---|---|---|---|
| Unprimed | Media | 1141.3 ± 201.3 | 446.1 ± 13.3 | 421.0 ± 21.0 |
| | IL-4 | 1176.0 ± 79.5 | 477.6 ± 30.8 | 393.5 ± 36.5 |
| | LPS/IFNγ | 1860.4 ± 140.6 | 1080.1 ± 113.1 | 1546.2 ± 196.5 |
| | UBM-ECM | 957.8 ± 42.8 | 461.4 ± 8.0 | 413.6 ± 67.1 |
| | MBV | 731.2 ± 33.4 | 463.1 ± 36.8 | 497.9 ± 53.1 |
| Primed | Media | 1642.0 ± 110.3 | 1013.2 ± 88.8 | 1165.7 ± 190.0 |
| | UBM-ECM | 893.9 ± 46.9 | 652.3 ± 55.8 | 517.2 ± 39.7 |
| | MBV | 671.5 ± 24.0 | 523.3 ± 136.9 | 678.7 ± 15.5 |

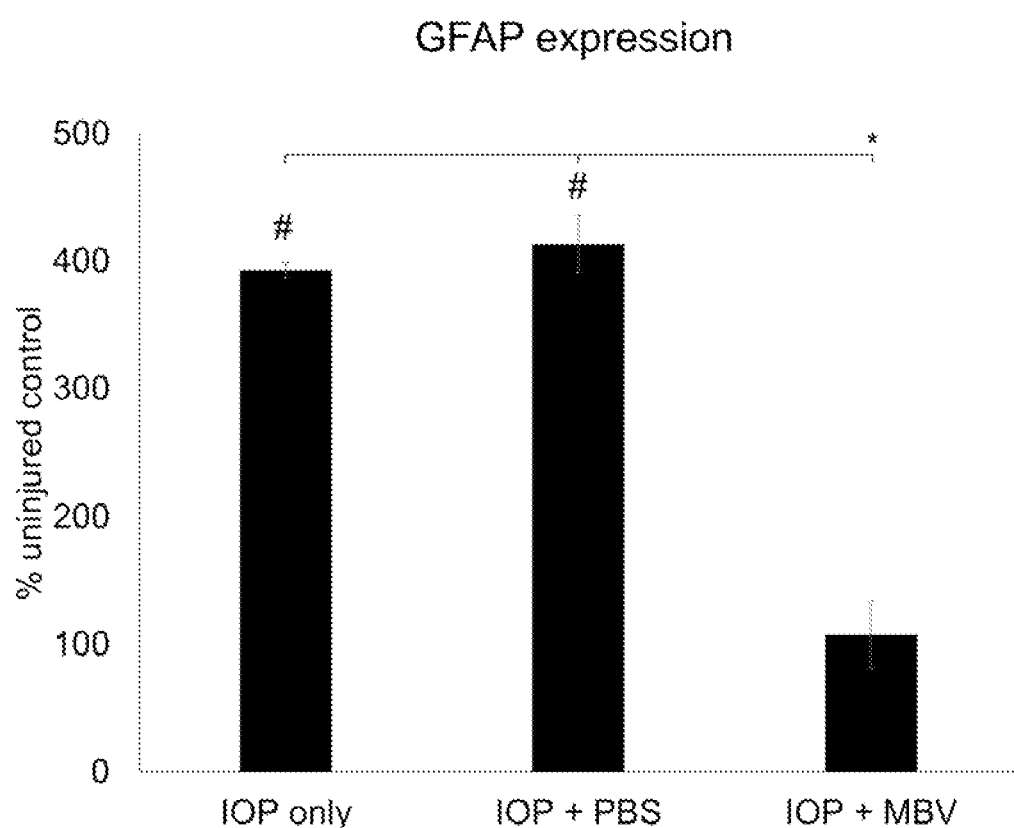

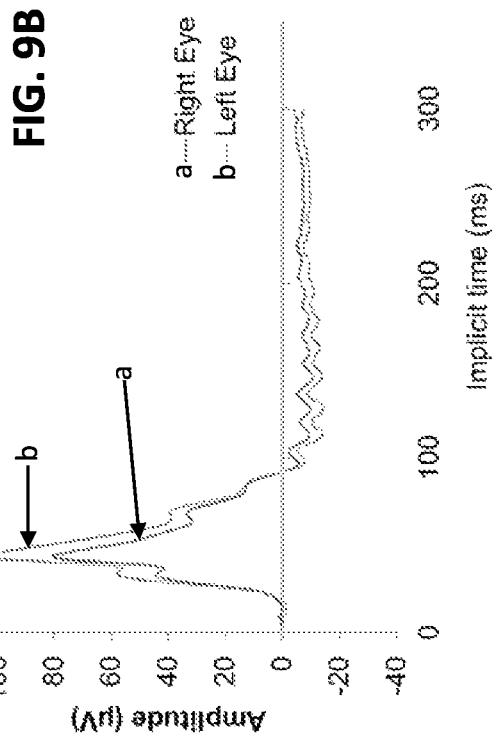
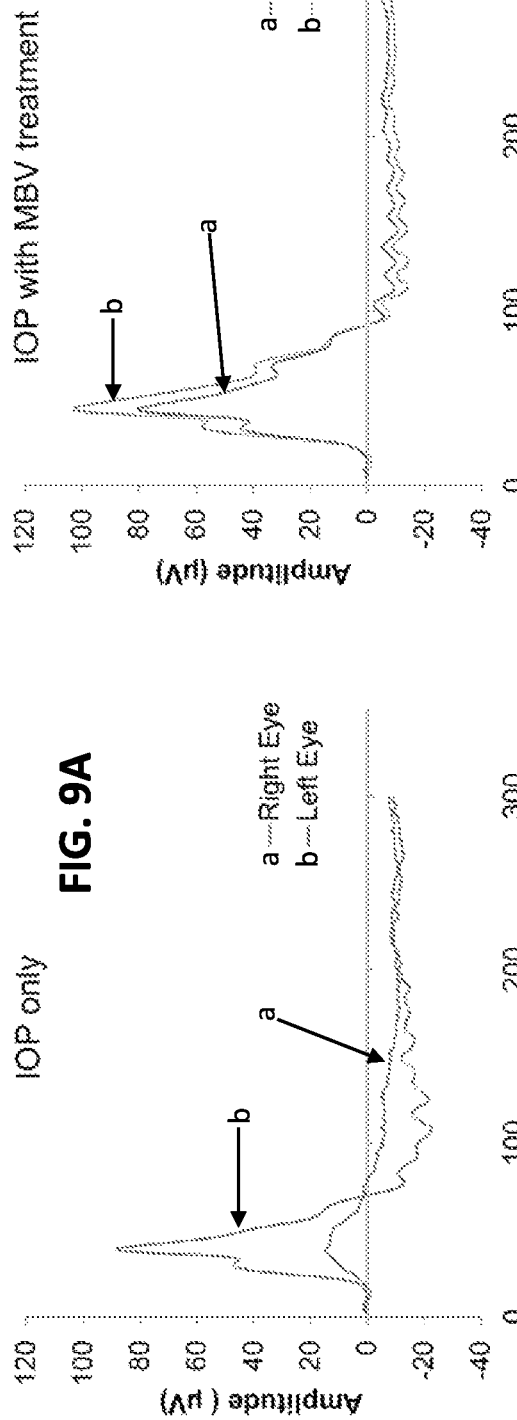
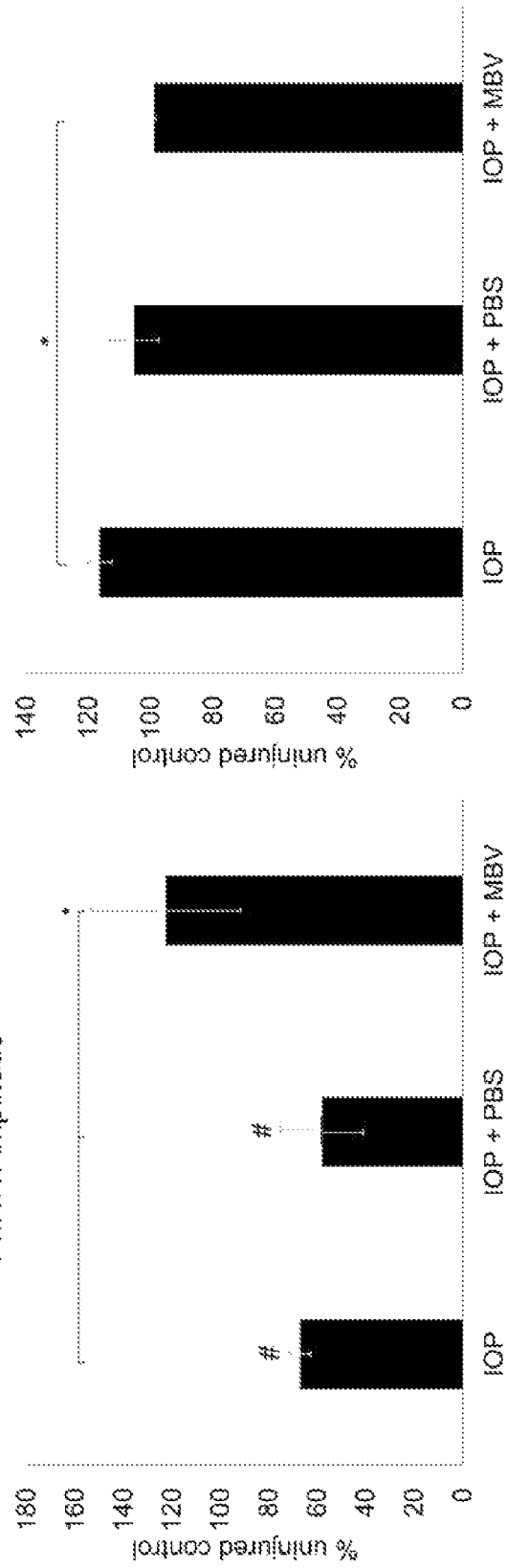

OCULAR APPLICATIONS OF MATRIX BOUND VESICLES (MBVS)

CROSS REFERENCE TO RELATED APPLICATION

This is a § 371 U.S. national stage of International Application No. PCT/US2018/031190, filed May 4, 2018, which claims the benefit of U.S. Provisional Application No. 62/502,271, filed May 5, 2017, which is incorporated herein by reference.

ACKNOWLEDGMENT OF GOVERNMENT SUPPORT

This invention was made with government support under grant no. W81XWH-15-1-0026 awarded by the United States Army/MRMC. The government has certain rights in the invention.

FIELD

This relates to the field of ophthalmology, specifically to the use of matrix bound nanovesicles (MBVs) to increase retinal ganglion cell (RGC) survival and the treatment of ophthalmic diseases associated with decreased RGC survival.

BACKGROUND

There is a large unmet need for therapies targeting nerve repair following ocular injuries and neurodegenerative diseases that implicate RGC death. Approximately 285 million people worldwide suffer from varying degrees of permanent vision loss (WHO, "Visual impairment and blindness." available on-line at who.int/mediacentre/factsheets/fs282/en/. August 2014) due to diseases or trauma to the eye. In the United States alone, 2 5 million cases of eye injury occur yearly of which 50,000 result in permanent blindness (Owens and Mutter, Statistical Brief #112. Healthcare Cost and Utilization Project (HCUP) Statistical Briefs. Rockville (Md.) 2006). Failed RGC axon regeneration remains a barrier to ocular repair due to the variety of injury-induced factors that suppress axon regeneration. These factors include poor intrinsic axon growth ability (Goldberg et al., Neuron 33(5): 689-702, 2002), lost neurotrophic support (Mansour-Robaey et al., Proc Natl Acad Sci USA 91(5): 1632-1636, 1994), inhibitory molecules expressed by glia (McKeon et al., J Neurosci 19(24): 10778-10788, 1999) or released during cellular injury (McKeon et al., J Neurosci 11(11): 3398-3411, 1991), and an inflammatory immune response (Darlington et al., J Neuropathol Exp Neurol 67(6): 590-599m 2008). In rodent models, multifactorial approaches targeting one or more of these factors by molecular or genetic manipulations can improve neuron survival and regeneration. However, using the currently available modalities, the number of neurons that regenerate successfully is low (Tropea et al., J Neurosci 23(18): 7034-7044, 2003) with poor target reinnervation and little to no functional recovery. Thus, a need remains for methods for regenerating axons, such as in the retinal ganglion.

Regenerative medicine strategies using extracellular matrix (ECM) technology have been successful, pre-clinically and clinically, in promoting tissue repair in the muscle and connective tissues. ECM is the unique protein and polysaccharide microenvironment that defines both cellular and tissue identities and functions. ECM technology uses xenogeneic ECM bioscaffolds, derived by decellularizing healthy tissues. Though the exact mechanisms are unknown, ECM bioscaffolds can increase anti-inflammatory, M2-like, signaling in macrophages and direct site-appropriate cellular recruitment and differentiation to decrease scarring and to increase site-appropriate tissue repair in tissues the body cannot repair by default. Recently, matrix bound vesicles (MBVs) have been found in all experimental and commercial ECM bioscaffolds tested, and preliminary data show that MBVs can recapitulate many of the positive effects of the parent ECM. A new use for MBVs is disclosed herein.

SUMMARY

Methods are disclosed herein for increasing retinal ganglion cell survival in a subject in need thereof. These methods include selecting a subject in need of increased retinal ganglion cell survival, and locally administering to an eye of the subject a therapeutically effective amount of isolated nanovesicles derived from an extracellular matrix, wherein the nanovesicles maintain expression of F4/80 and CD-11b on macrophages in the subject, wherein the nanovesicles comprise lysyl oxidase, and wherein the nanovesicles a) do not express CD63 or CD81, or b) are $CD63^{lo}CD81^{lo}$.

Disclosed herein is the use of a composition comprising a therapeutically effective amount of isolated nanovesicles derived from an extracellular matrix, wherein the nanovesicles maintain expression of F4/80 and CD-11b on macrophages in the subject, wherein the nanovesicles comprise lysyl oxidase, and wherein the nanovesicles a) do not express CD63 or CD81, or b) are $CD63^{lo}CD$, for increasing retinal ganglion cell suvival. In some embodiments, these compositions are of use for treating a subject with glaucoma. In further embodiments, these compositions are of use for treating a subject with retinal ganglion cell degeneration caused by injury or a genetic disorder. In more embodiments, these compositions are of use for treating a subject that has pressure-independent glaucomatous optic neuropathy, ischemic optic neuropathy, inflammatory optic neuropathy, compressive optic neuropathy, or traumatic optic neuropathy. In other embodiments, these compositions are of use for treating a subject that has has arteritic ischemic optic neuropathy, arteritic ischemic optic neuropathy associated with giant cell arteritis, nonarteritic ischemic optic neuropathy, infiltrative optic neuropathy, infiltrative optic neuropathy associated with sarcoidosis, infectious optic neuropathy, infectious optic neuropathy associated with syphilis, infectious optic neuropathy associated with Lyme disease, infectious optic neuropathy associated with toxoplasmosis, infectious optic neuropathy associated with herpes zoster, optic neuritis from demyelinating disease, postradiation optic neuropathy, acrodermatitis enteropathica, hereditary optic neuropathy, hereditary optic neuropathy associated with dominant optic neuropathy, compressive optic neuropathy, compressive optic neuropathy associated with orbital pseudotumor, compressive optic neuropathy associated with thyroid eye disease, autoimmune optic neuropathy, or autoimmune optic neuropathy associated with Lupus.

The foregoing and other objects, features, and advantages of the invention will become more apparent from the following detailed description, which proceeds with reference to the accompanying figures.

BRIEF DESCRIPTION OF THE DRAWINGS

FIGS. 2A-2H. MBV suppress pro-inflammatory cytokine secretion from both microglia and astrocyte. (A-C) In unprimed microglia, LPS/IFNγ increased the proinflammatory cytokines. In primed microglia, IL-1β, IL-6, and TNF-α secretion remained elevated in media but the secretion of all three cytokines was reduced significantly by both UBM-ECM and MBV. (D-F) Similar to microglia, LPS/IFNγ increased pro-inflammatory cytokine secetion from astrocytes and these increases were decreased by both UBM-ECM and MBV. (G-H) Tables show actual cytokine concentrations for both unprimed and primed microglia (G) and astrocytes (H). Error bars represent SEM, data represent triplicate samples from three independent experiments. One-way ANOVA between groups, *p<0.05.

FIGS. 7A-7B. MBV decrease IOP-induced glial fibrillar acidic protein (GFAP) expression in the optic nerve. (A) Representative images showing GFAP expression in the optic nerve of uninjured control eyes (control), untreated IOP eyes (IOP), PBS treated IOP eyes, and MBV treated IOP eyes. (B) Quantitative analysis of GFAP immunoreactivity showed intravitreal MBV injections reduce GFAP expression in the optic nerve. Error bars represent SEM, n=5 animals per groups, 15 images per optic nerve, totaling 75 images analyzed per group. Significance was determined by one-way ANOVA with Post-hoc Tukey's test between groups; #p<0.001, compared to media; *p<0.001 between groups.

FIGS. 9A-9D. MBV injection after ischemic injury increases Photopic negative response (PhNR) amplitude and shortens latency. (A) Comparison of the electroretinography (ERG) response in an uninjured retina (blue line) or IOP-injured retina (red line) 14 days after IOP elevation. (B) Comparison of the ERG response in an uninjured retina (blue line) or the retina of an MBV-treated eye following IOP injury (red line), 14 days after IOP elevation. (C) Quantitatively, IOP elevation with and without PBS injection decreased the photopic negative response (PhNR) amplitude compared to the uninjured control. MBV treatment increased the PhNR amplitude compared to untreated groups and there was no difference in PhNR amplitude between uninjured and MBV treated groups. (D) IOP elevation decreased latency of the PhNR and was significantly increased compared to IOP elevation with MBV treatment. C, D. Error bars represent SEM, n=5 animals per groups, 3 ERG recordings per animals. Significance was determined by one-way ANOVA with Post-hoc Tukey's test between groups; #p<0.05, compared to media; *p<0.05 between groups.

SEQUENCE LISTING

Figure 1A:
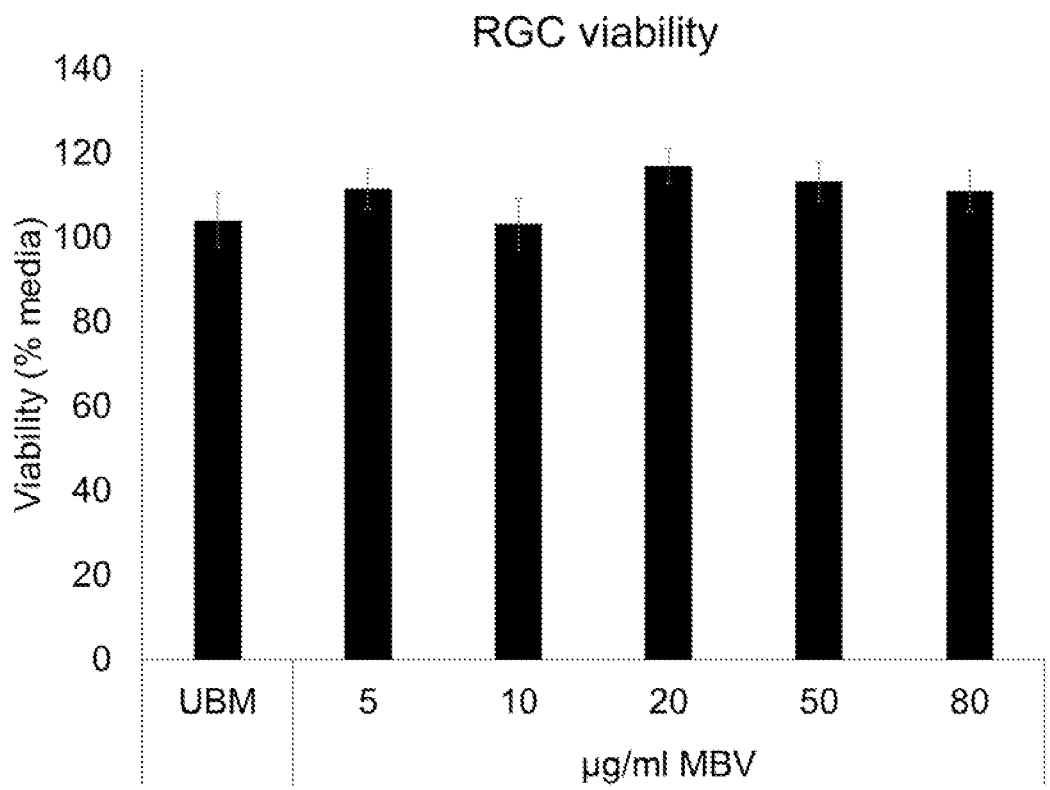
FIGS. 1A-1B. MBV increase RGC neurite growth. (A) RGC viability was unchanged by either UBM-ECM or MBV (5-80 µg/ml). Data was normalized to no treatment control. (B) Total RGC neurite growth increased with MBV treatment (5-20) µg/ml, and decreased with MBV doses of 50-80 µg/ml. Error bars indicate the SEM, n=3. *p<0.01 compared to media; **p<0.001 compared to media.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [8123-100511-09_Sequence Listing Nov. 4, 2019, 1.16 KB], which is incorporated by reference herein.

DETAILED DESCRIPTION

Biologic scaffolds composed of extracellular matrix (ECM) have been developed as surgical mesh materials and are used in clinical applications including ventral hernia repair (Alicuban et al., Hernia. 2014; 18(5):705-712), musculoskeletal reconstruction (Mase et al., Orthopedics. 2010; 33(7):511), esophageal reconstruction (Badylak et al., Tissue Eng Part A. 2011; 17(11-12):1643-50), dura mater replacement (Bejjani et al., J Neurosurg. 2007; 106(6):1028-1033), tendon repair (Longo et al., Stem Cells Int. 2012; 2012:517165), breast reconstruction (Salzber, Ann Plast Surg. 2006; 57(1):1-5), amongst others (Badylak et al., Acta Biomater. 2009; 5(1):1-13).

Matrix bound nanovesicles (MBVs) are embedded within the fibrillar network of the ECM. These nanoparticles shield their cargo from degradation and denaturation during the ECM-scaffold manufacturing process. Exosomes are microvesicles that previously have been identified almost exclusively in body fluids and cell culture supernatant. It has been demonstrated that MBVs and exosomes are distinct. The MBV differ from other microvesicles, for example, as they are resistant to detergent and/or enzymatic digestion, contain a cluster of different microRNAs, and are enriched in miR-145. MBV$^s$ do not have characteristic surface proteins found in other microvesicles such as exosomes. As disclosed herein, MBVs affect cellular survival an modulate a healing response to preserve or to restore neurologic function. It is disclosed that MBVs differentially regulate RGC survival, axon growth, and tissue remodeling.

Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GENBANK® Accession Nos. referred to herein are the sequences available at least as early as Sep. 16, 2015. All references, patent applications and publications, and GENBANK® Accession numbers cited herein are incorporated by reference. In order to facilitate review of the various embodiments of the disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Biocompatible: Any material, that, when implanted in a mammalian subject, does not provoke an adverse response in the subject. A biocompatible material, when introduced into an individual, is able to perform its' intended function, and is not toxic or injurious to that individual, nor does it induce immunological rejection of the material in the subject.

Enriched: A process whereby a component of interest, such as a nanovesicle, that is in a mixture has an increased ratio of the amount of that component to the amount of other undesired components in that mixture after the enriching process as compared to before the enriching process.

Extracellular matrix (ECM): A complex mixture of structural and functional biomolecules and/or biomacromolecules including, but not limited to, structural proteins, specialized proteins, proteoglycans, glycosaminoglycans, and growth factors that surround and support cells within tissues and, unless otherwise indicated, is acellular. ECM preparations can be considered to be "decellularized" or "acellular", meaning the cells have been removed from the source tissue through processes described herein and known in the art. By "ECM-derived material," such as an "ECM-derivied nanovesicle," "Matrix bound nanovesicle," "MBV" or "nanovesicle derived from an ECM" it is a nanovesicle that is prepared from a natural ECM or from an in vitro source wherein the ECM is produced by cultured cells. ECM-derived nanovesicles are defined below.

Glaucoma: An eye disorder characterized by retinal ganglion cell death, excavation of the optic nerve head and gradual loss of the visual field. An abnormally high intraocular pressure is commonly known to be detrimental to the eye and is one of the main risk factors in glaucoma. In glaucoma patients, high intraocular pressure can result in degenerative changes in the retina. "Ocular hypertension" refers to clinical situation in individuals with an abnormally high intraocular pressure without any manifestation of defects in the visual field or optic nerve head. Individuals with ocular hypertension carry the risk of conversion to glaucoma with the risk being correlated to higher intraocular pressure measurements.

Glaucoma can be divided into open-angle form and the closed-angle forms and further classified into acute and chronic forms. There also is a normal-tension glaucoma. The glaucoma can be a primary or a secondary glaucoma. More than 80% of all glaucoma cases are chronic open angle glaucoma (COAG), also called primary open angle glaucoma. Any of these forms of glaucoma can be treated using the methods disclosed herein.

"Primary angle closure glaucoma" is caused by contact between the iris, trabecular meshwork, and peripheral cornea which in turn obstructs outflow of the aqueous humor from the eye. This contact between iris and trabecular meshwork (TM) may gradually damage the function of the meshwork until it fails to keep pace with aqueous production, and the pressure rises. In over half of all cases, prolonged contact between iris and TM causes the formation of synechiae (effectively "scars"). These cause permanent obstruction of aqueous outflow. In some cases, pressure may rapidly build up in the eye, causing pain and redness (symptomatic, or so-called "acute" angle closure). In this situation, the vision may become blurred, and halos may be seen around bright lights. Accompanying symptoms may include a headache and vomiting. Diagnosis can made from physical signs and symptoms: pupils mid-dilated and unresponsive to light, cornea edematous (cloudy), reduced vision, redness, and pain. However, the majority of cases are asymptomatic. Prior to the very severe loss of vision, these cases can only be identified by examination, generally by an eye care professional.

"Primary open-angle glaucoma" occurs when optic nerve damage results in a progressive loss of the visual field. Not all people with primary open-angle glaucoma have eye pressure that is elevated beyond normal. The increased pressure is caused by the blockage of the aqueous humor outflow pathway. Because the microscopic passageways are blocked, the pressure builds up in the eye and causes imperceptible very gradual vision loss. Peripheral vision is affected first, but eventually the entire vision will be lost if not treated. Diagnosis can be made by looking for cupping of the optic nerve and measuring visual field. Prostaglandin agonists work by opening uveoscleral passageways.

Other forms of glaucoma are developmental glaucoma and secondary glaucoma, which can occur after uveitis, iridocyclitis, intraocular hemorrhage, trauma, or an intraocular tumor. Any form of glaucoma can be treated using the methods disclosed herein.

The death of retinal ganglion cells occurs in glaucoma. Methods are disclosed herein for increasing the survival of retinal ganglion cells.

Intraocular administration: Administering agents directly into the eye, for example by delivery into the vitreous or anterior chamber. Indirect intraocular delivery (for example by diffusion through the cornea) is not direct administration into the eye.

Intraocular Pressure: The pressure of the fluid that fills the eye globe, the aqueous humor, which is determined by the interplay between the rate of aqueous humor production inside the eye and the resistance to aqueous outflow as it exits the eye through the anterior chamber angle towards Schlemm's canal. In the human eye, the rate of aqueous formation is 2.54/minute while that in the rabbit eye is approximately 3 to 4 µL/minute. Normal IOP measurements in the human eye, according to widely acceptable consensus, range between 10 and 20 mm of mercury, with an average of 15.5 mm.

Intravitreal administration: Administering agents into the vitreous cavity. The vitreous cavity is the space that occupies most of the volume of the core of the eye with the lens and its suspension system (the zonules) as its anterior border and the retina and its coating as the peripheral border. Intravitreal administration can be accomplished by injection, pumping, or by implants.

Isolated: An "isolated" biological component (such as a nucleic acid, protein cell, or nanovesicle) has been substantially separated or purified away from other biological components in the cell of the organism or the ECM, in which the component naturally occurs. Nucleic acids and proteins that have been "isolated" include nucleic acids and proteins purified by standard purification methods. Nanovesicles that have been isolated are removed from the fibrous materials of the ECM. The term also embraces nucleic acids and proteins prepared by recombinant expression in a host cell as well as chemically synthesized nucleic acids.

Lysyl oxidase (Lox): A copper-dependent enzyme that catalyzes formation of aldehydes from lysine residues in collagen and elastin precursors. These aldehydes are highly reactive, and undergo spontaneous chemical reactions with other lysyl oxidase-derived aldehyde residues, or with unmodified lysine residues. In vivo, this results in cross-linking of collagen and elastin, which plays a role in stabilization of collagen fibrils and for the integrity and elasticity of mature elastin. Complex cross-links are formed in collagen (pyridinolines derived from three lysine residues) and in elastin (desmosines derived from four lysine residues) that differ in structure. The genes encoding Lox enzymes have been cloned from a variety of organisms (Hamalainen et al., Genomics 11:508, 1991; Trackman et al., Biochemistry 29:4863, 1990; incorporated herein by reference). Residues 153-417 and residues 201-417 of the sequence of human lysyl oxidase have been shown to be important for catalytic function. There are four Lox-like isoforms, called LoxL1, LoxL2, LoxL3 and LoxL4.

Macrophage: A type of white blood cell that phagocytoses and degrades cellular debris, foreign substances, microbes, and cancer cells. In addition to their role in phagocytosis, these cells play an important role in development, tissue maintenance and repair, and in both innate and adaptive immunity in that they recruit and influence other cells including immune cells such as lymphocytes. Macrophages can exist in many phenotypes, including phenotypes that have been referred to as M1 and M2. Macrophages that perform primarily pro-inflammatory functions are called M1 macrophages (CD86+/CD68+), whereas macrophages that decrease inflammation and encourage and regulate tissue repair are called M2 macrophages (CD206+/CD68+). The markers that identify the various phenotypes of macrophages vary among species. It should be noted that macrophage phenotype is represented by a spectrum that ranges between the extremes of M1 and M2. F4/80 (encoded by the adhesion G protein coupled receptor E1 (ADGRE1) gene) is a macrophage marker, see GENBANK® Accession No. NP_001243181.1, Apr. 6, 2018 and NP_001965, Mar. 5, 2018, both incorporated herein by reference.

MicroRNA: A small non-coding RNA that is about 17 to about 25 nucleotide bases in length, that post-transcriptionally regulates gene expression by typically repressing target mRNA translation. A miRNA can function as negative regulators, such that greater amounts of a specific miRNA will correlates with lower levels of target gene expression. There are three forms of miRNAs, primary miRNAs (pri-miRNAs), premature miRNAs (pre-miRNAs), and mature miRNAs. Primary miRNAs (pri-miRNAs) are expressed as stem-loop structured transcripts of about a few hundred bases to over 1 kb. The pri-miRNA transcripts are cleaved in the nucleus by an RNase II endonuclease called Drosha that cleaves both strands of the stem near the base of the stem loop. Drosha cleaves the RNA duplex with staggered cuts, leaving a 5' phosphate and 2 nucleotide overhang at the 3' end. The cleavage product, the premature miRNA (pre-miRNA) is about 60 to about 110 nucleotides long with a hairpin structure formed in a fold-back manner Pre-miRNA is transported from the nucleus to the cytoplasm by Ran-GTP and Exportin-5. Pre-miRNAs are processed further in the cytoplasm by another RNase II endonuclease called Dicer. Dicer recognizes the 5' phosphate and 3' overhang, and cleaves the loop off at the stem-loop junction to form miRNA duplexes. The miRNA duplex binds to the RNA-induced silencing complex (RISC), where the antisense strand is preferentially degraded and the sense strand mature miRNA directs RISC to its target site. It is the mature miRNA that is the biologically active form of the miRNA and is about 17 to about 25 nucleotides in length.

Nanovesicle: An extracellular vesicle that is a nanoparticle of about 10 to about 1,000 nm in diameter. Nanovesicles are lipid membrane bound particles that carry biologically active signaling molecules (e.g. microRNAs, proteins) among other molecules. Generally, the nanovesicle is limited by a lipid bilayer, and the biological molecules are enclosed and/or can be embedded in the bilayer. Thus, a nanovesicle includes a lumen surrounded by plasma membrane. The different types of vesicles can be distinguished based on diameter, subcellular origin, density, shape, sedimentation rate, lipid composition, protein markers, nucleic acid content and origin, such as from the extracellular matrix or secreted. A nanovesicle can be identified by its origin, such as a matrix bound nanovesicle from an ECM (see above), protein content and/or the miR content.

An "exosome" is a membranous vesicle which is secreted by a cell, and ranges in diameter from 10 to 150 nm. Generally, late endosomes or multivesicular bodies contain intralumenal vesicles which are formed by the inward budding and scission of vesicles from the limited endosomal membrane into these enclosed vesicles. These intralumenal vesicles are then released from the multivesicular body lumen into the extracellular environment, typically into a body fluid such as blood, cerebrospinal fluid or saliva, during exocytosis upon fusion with the plasma membrane. An exosome is created intracellularly when a segment of membrane invaginates and is endocytosed. The internalized segments which are broken into smaller vesicles and ultimately expelled from the cell contain proteins and RNA molecules such as mRNA and miRNA. Plasma-derived exosomes largely lack ribosomal RNA. Extra-cellular matrix derived exosomes include specific miRNA and protein components, and have been shown to be present in virtually every body fluid such as blood, urine, saliva, semen, and cerebrospinal fluid. Exosomes can express CD11c and CD63, and thus can be CD11c$^+$ and CD63$^+$. Exosomes do not have high levels of lysl oxidase on their surface.

A "nanovesicle derived from an ECM" "matrix bound nanovesicle," "MBV" or an "ECM-derived nanovesicle" all refer to the same membrane bound particles, ranging in size from 10 nm-1000 nm, present in the extracellular matrix, which contain biologically active signaling molecules such as protein, lipids, nucleic acid, growth factors and cytokines that influence cell behavior. The terms are interchangeable, and refer to the same vesicles. These MBVs are embedded within, and bound to, the ECM and are not just attached to the surface. These MBVs are resistant harsh isolation conditions, such as freeze thawing and digestion with proteases such as pepsin, elastase, hyaluronidase, proteinase K, and collagenase, and digestion with detergents. Generally, these MBVs are enriched for miR-145 and optionally miR-181, miR-143, and miR-125, amongst others. These MBVs do not express CD63 or CD81, or express barely detectable levels of these markers)(CD63$^{lo}$CD81$^{lo}$. The MBVs contain lysl oxidase (Lox) on their surface. The ECM can be an ECM from a tissue, can be produced from cells in culture, or can be purchased from a commercial source. MBVs are distinct from exosomes.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell.

"Incubating" includes a sufficient amount of time for a drug to interact with a cell. "Contacting" includes incubating an agent, such as an exosome, a miRNA, or nucleic acid encoding a miRNA, in solid or in liquid form with a cell.

Phototoxicity: Damage to cells induced by light.

Polynucleotide: A nucleic acid sequence (such as a linear sequence) of any length. Therefore, a polynucleotide includes oligonucleotides, and also gene sequences found in chromosomes. An "oligonucleotide" is a plurality of joined nucleotides joined by native phosphodiester bonds. An oligonucleotide is a polynucleotide of between 6 and 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Purified: The term "purified" does not require absolute purity; rather, it is intended as a relative term. Thus, for example, a purified nucleic acid molecule preparation is one in which the nucleic referred to is more pure than the nucleic in its natural environment within a cell. For example, a preparation of a nucleic acid is purified such that the nucleic acid represents at least 50% of the total protein content of the preparation. Similarly, a purified exosome preparation is one in which the exosome is more pure than in an environment including cells, wherein there are microvesicles and exosomes. A purified population of nucleic acids or exosomes is greater than about 90%, 91%, 92%, 93%, 94%, 95%, 96%, 97%, 98%, 99% or 100% pure, or free other nucleic acids or cellular components, respectively.

Preventing or treating a disease: "Preventing" a disease refers to inhibiting the development of a disease, for example in a person who is known to have a predisposition to a disease such as gaucoma. An example of a person with a known predisposition is someone with a history of a disease in the family, or who has been exposed to factors that predispose the subject to a condition. "Treatment" refers to a therapeutic intervention that ameliorates a sign or symptom of a disease or pathological condition after it has begun to develop.

Retina: The light (photon) sensitive portion of the eye, that contains the photoreceptors (cones and rods) for light. Rods and cones perform light perception through the use of light sensitive pigments. The light sensitive pigments are made of protein called opsin and a chromophore called retinene, which the variant is of vitamin A The rods contain rhodopsin while the cones contains iodopsin. Rods and cones transmit signals through successive neurons that trigger a neural discharge in the output cells of the retina and the ganglion cells. The visual signals are conveyed by the optic nerve to the lateral geniculate bodies from where the visual signal is passed to the visual cortex (occipital lobe) and registered as a visual stimulus.

Subject: Human and non-human animals, including all vertebrates, such as mammals and non-mammals, such as non-human primates, mice, rabbits, sheep, dogs, cats, horses, cows, chickens, amphibians, and reptiles. In many embodiments of the described methods, the subject is a human.

Therapeutically effective amount: A quantity of a specific substance, such as an MBV, sufficient to achieve a desired effect in a subject being treated. When administered to a subject, a dosage will generally be used that will achieve target tissue concentrations (for example, in bone) that has been shown to achieve a desired in vitro effect.

Transplanting: The placement of a biocompatible substrate, such as an MBV, into a subject in need thereof.

Treating, Treatment, and Therapy: Any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or improving vision. The treatment may be assessed by objective or subjective parameters; including the results of a physical examination, neurological examination, or psychiatric evaluations.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Nanovesicles Derived from an Extracellular Matrix (ECM)

Nanovesicles derived from ECM (also called matrix bound nanovesicles, MBVs) are disclosed in PCT Publication No. WO 2017/151862, which is incorporated herein by reference. It is disclosed that nanovesicles are embedded in the extracellular matrix. These MBVs can be isolated and are biologically active. Thus, these MBVs can be used for therapeutic purposes, either alone or with another ECM. These MBVs can be used in biological scaffolds, either alone or with another ECM.

An extracellular matrix is a complex mixture of structural and functional biomolecules and/or biomacromolecules including, but not limited to, structural proteins, specialized proteins, proteoglycans, glycosaminoglycans, and growth factors that surround and support cells within mammalian tissues and, unless otherwise indicated, is acellular. Generally, the disclosed MBVs are embedded in any type of extracellular matrix (ECM), and can be isolated from this location. Thus, MBVs are not detachably present on the surface of the ECM, and are not exosomes.

Extracellular matrices are disclosed, for example and without limitation, in U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666; each of which is incorporated by reference in its entirety). However, an ECM can be produced from any tissue, or from any in vitro source wherein the ECM is produced by cultured cells and comprises one or more polymeric components (constituents) of native ECM. ECM preparations can be considered to be "decellularized" or "acellular", meaning the cells have been removed from the source tissue or culture.

In some embodiments, the ECM is isolated from a vertebrate animal, for example, from a mammalian vertebrate animal including, but not limited to, human, monkey, pig, cow, sheep, etc. The ECM may be derived from any organ or tissue, including without limitation, urinary bladder, intestine, liver, heart, esophagus, spleen, stomach and dermis. In specific non-limiting examples, the extracellular matrix is isolated from esophageal tissue, urinary bladder, small intestinal submucosa, dermis, umbilical cord, pericardium, cardiac tissue, or skeletal muscle. The ECM can comprise any portion or tissue obtained from an organ, including, for example and without limitation, submucosa, epithelial basement membrane, tunica propria, etc. In one non-limiting embodiment, the ECM is isolated from urinary bladder.

The ECM may or may not include the basement membrane. In another non-limiting embodiment, the ECM includes at least a portion of the basement membrane. The ECM material may or may not retain some of the cellular elements that comprised the original tissue such as capillary endothelial cells or fibrocytes. In some embodiments, the ECM contains both a basement membrane surface and a non-basement membrane surface.

In one non-limiting embodiment, the ECM is harvested from porcine urinary bladders (also known as urinary bladder matrix or UBM). Briefly, the ECM is prepared by removing the urinary bladder tissue from a mammal, such as a pig, and trimming residual external connective tissues, including adipose tissue. All residual urine is removed by repeated washes with tap water. The tissue is delaminated by first soaking the tissue in a deepithelializing solution, for example and without limitation, hypertonic saline (e.g. 1.0 N saline), for periods of time ranging from ten minutes to four hours. Exposure to hypertonic saline solution removes the epithelial cells from the underlying basement membrane. Optionally, a calcium chelating agent may be added to the saline solution. The tissue remaining after the initial delamination procedure includes the epithelial basement membrane and tissue layers abluminal to the epithelial basement membrane. The relatively fragile epithelial basement membrane is invariably damaged and removed by any mechanical abrasion on the luminal surface. This tissue is next subjected to further treatment to remove most of the abluminal tissues but maintain the epithelial basement membrane and the tunica propria. The outer serosal, adventitial, tunica muscularis mucosa, tunica submucosa and most of the muscularis mucosa are removed from the remaining deepithelialized tissue by mechanical abrasion or by a combination of enzymatic treatment (e.g., using trypsin or collagenase) followed by hydration, and abrasion. Mechanical removal of these tissues is accomplished by removal of mesenteric tissues with, for example and without limitation, Adson-Brown forceps and Metzenbaum scissors and wiping away the tunica muscularis and tunica submucosa using a longitudinal wiping motion with a scalpel handle or other rigid object wrapped in moistened gauze. Automated robotic procedures involving cutting blades, lasers and other methods of tissue separation are also contemplated. After these tissues are removed, the resulting ECM consists mainly of epithelial basement membrane and subjacent tunica propria.

In another embodiment, the ECM is prepared by abrading porcine bladder tissue to remove the outer layers including both the tunica serosa and the tunica muscularis using a longitudinal wiping motion with a scalpel handle and moistened gauze. Following eversion of the tissue segment, the luminal portion of the tunica mucosa is delaminated from the underlying tissue using the same wiping motion. Care is taken to prevent perforation of the submucosa. After these tissues are removed, the resulting ECM consists mainly of the tunica submucosa (see FIG. 2 of U.S. Pat. No. 9,277,999, which is incorporated herein by reference).

ECM can also be prepared as a powder. Such powder can be made according the method of Gilbert et al., Biomaterials 26 (2005) 1431-1435, herein incorporated by reference in its entirety. For example, UBM sheets can be lyophilized and then chopped into small sheets for immersion in liquid nitrogen. The snap frozen material can then be comminuted so that particles are small enough to be placed in a rotary knife mill, where the ECM is powdered. Similarly, by precipitating NaCl within the ECM tissue the material will fracture into uniformly sized particles, which can be snap frozen, lyophilized, and powdered.

In one non-limiting embodiment, the ECM is derived from small intestinal submucosa or SIS. Commercially available preparations include, but are not limited to, SUR-GISIS™, SURGISIS-ES™, STRATASIS™, and STRATA-SIS-ES™ (Cook Urological Inc.; Indianapolis, Ind.) and GRAFTPATCH™ (Organogenesis Inc.; Canton Mass.). In another non-limiting embodiment, the ECM is derived from dermis. Commercially available preparations include, but are not limited to PELVICOL™ (sold as PERMACOL™ in Europe; Bard, Covington, Ga.), REPLIFORM™ (Microvasive; Boston, Mass.) and ALLODERM™ (LifeCell; Branchburg, N.J.). In another embodiment, the ECM is derived from urinary bladder. Commercially available preparations include, but are not limited to UBM (ACell Corporation; Jessup, Md.).

MBVs can be derived from (released from) an extracellular matrix using the methods disclosed below. In some embodiments, the ECM is digested with an enzyme, such as pepsin, collagenase, elastase, hyaluronidase, or proteinase K, and the MBVs are isolated. In other embodiments, the MBVs are released and separated from the ECM by changing the pH with solutions such as glycine HCL, citric acid, ammonium hydroxide, use of chelating agents such as, but not limited to, EDTA, EGTA, by ionic strength and or chaotropic effects with the use of salts such as, but not limited to potassium chloride (KCl), sodium chloride, magnesium chloride, sodium iodide, sodium thiocyanate, or by exposing ECM to denaturing conditions like guanidine HCl or Urea.

In particular examples, the MBVs are prepared following digestion of an ECM with an enzyme, such as pepsin, elastase, hyaluronidase, proteinase K, salt solutions, or collagenase. The ECM can be freeze-thawed, or subject to mechanical degradation.

In some embodiments, expression of CD63 and/or CD81 cannot be detected on the MBVs. Thus, the MBVs do not express CD63 and/or CD81. In a specific example, both CD63 and CD81 cannot be detected on the nanovesicles. In other embodiments, the MBVs have barely detectable levels of CD63 and CD81, such as that detectable by Western blot. These MBVs are CD63$^{lo}$CD81$^{lo}$. One of skill in the art can readily identify MBVs that are CD63$^{lo}$CD81$^{lo}$, using, for example, antibodies that specifically bind CD63 and CD81. A low level of these markers can be established using procedures such as fluorescent activated cell sorting (FACS) and fluorescently labeled antibodies to determine a threshold for low and high amounts of CD63 and CD81. The disclosed MBVs differ from nanovesicles, such as exosomes that may be transiently attached to the surface of the ECM due to their presence in biological fluids.

The MBVs include lysloxidase oxidase (Lox). Generally, nanovesicles derived from the ECM have a higher Lox content than exosomes. Lox is expressed on the surface of MBVs. Nano-LC MS/MS proteomic analysis can be used to detect Lox proteins. Quantification of Lox can be performed as previously described (Hill R C, et al., Mol Cell Proteomics. 2015; 14(4):961-73).

In certain embodiments, the MBVs comprise one or more miRNA. In specific non-limiting examples, the MBVs comprise one, two, or all three of miR-143, miR-145 and miR-181. MiR-143, miR-145 and miR-181 are known in the art.

The miR-145 nucleic acid sequence is provided in MiRbase Accession No. MI0000461, incorporated herein by reference. A miR-145 nucleic acid sequence is CACCUUGUCCUCACGGUCCAGUUUUCCCAGGAAUCCC-UUAGAUGCUAAGAUGGGGA UUCCUGGAAAUA-CUGUUCUUGAGGUCAUGGUU (SEQ ID NO: 1). An miR-181 nucleic acid sequence is provided in miRbase Accession No. MI0000269, incorporated herein by reference. A miR-181 nucleic acid sequence is: AGAAGGGC-UAUCAGGCCAGCCUUCAGAGGACUCCAAGGAA-CAUUCAACGCUGUCGG UGAGUUUGGGAUUUGAAAAAACCA-CUGACCGUUGACUGUACCUUGGGGUCCUUA (SEQ ID NO: 2). The miR-143 nucleic acid sequence is provided in NCBI Accession No. NR_029684.1, Mar. 30, 2018, incorporated herein by reference. A DNA encoding an miR-143 nucleic acid sequence is: GCGCAGCGCC CTGTCTCCCA GCCTGAGGTG CAGTGCTGCA TCTCTGGTCA GTTGGGAGTC TGAGATGAAG CACTGTAGCT CAGGAAGAGA GAAGTTGTTC TGCAGC (SEQ ID NO: 3).

Following administration, the MBVs maintain expression of F4/80 (a macrophage marker) and CD-11b on macrophages in the subject. Nanovesicle treated macrophages are predominantly F4/80+Fizz1+indicating an M2 phenotype.

The MBVs disclosed herein can be formulated into compositions for pharmaceutical delivery, and used in bioscaffolds and devices. The MBVs are disclosed in PCT Publication No. WO 2017/151862, which is incorporated herein by reference.

Isolation of MBVs from the ECM

To produce MBVs, ECM can be produced by any cells of interest, or can be utilized from a commercial source, see above. The MBVs can be produced from the same species, or a different species, than the subject being treated. In some embodiments, these methods include digesting the ECM with an enzyme to produce digested ECM. In specific embodiments, the ECM is digested with one or more of pepsin, elastase, hyaluronidase, collagenase a metalloproteinase, and/or proteinase K. In a specific non-limiting example, the ECM is digested with only elastase and/or a metalloproteinase. In another non-limiting example, the ECM is not digested with collagenase and/or trypsin and/or proteinase K. In other embodiments, the ECM is treated with a detergent. In further embodiments, the method does not include the use of enzymes. In specific non-limiting examples, the method utilizes chaotropic agents or ionic strength to isolate MBVs such as salts, such as potassium chloride. In additional embodiments, the ECM can be manipulated to increase MBV content prior to isolation of MBVs.

In some embodiments, the ECM is digested with an enzyme. The ECM can be digested with the enzyme for about 12 to about 48 hours, such as about 12 to about 36 hours. The ECM can be digested with the enzyme for about 12, about 24 about 36 or about 48 hours. In one specific non-limiting example, the ECM is digested with the enzyme at room temperature. However, the digestion can occur at about 4° C., or any temperature between about 4° C. and 25° C. Generally, the ECM is digested with the enzyme for any length of time, and at any temperature, sufficient to remove collagen fibrils. The digestion process can be varied depending on the tissue source. Optionally, the ECM is processed by freezing and thawing, either before or after digestion with the enzyme. The ECM can be treated with detergents, including ionic and/or non-ionic detergents.

The digested ECM is then processed, such as by centrifugation, to isolate a fibril-free supernatant. In some embodiments the digested ECM is centrifuged, for example, for a first step at about 300 to about 1000 g. Thus, the digested ECM can be centrifuged at about 400 g to about 750 g, such as at about 400 g, about 450 g, about 500 g or about 600 g. This centrifugation can occur for about 10 to about 15 minutes, such as for about 10 to about 12 minutes, such as for about 10, about 11, about 12, about 14, about 14, or about 15 minutes. The supernatant including the digested ECM is collected.

The MBVs include Lox. In some embodiments, methods for isolating such MBVs include digesting the extracellular matrix with elastase and/or metalloproteinase to produce digested extracellular matrix, centrifuging the digested extracellular matrix to remove collagen fibril remnants and thus to produce a fibril-free supernatant, centrifuging the fibril-free supernatant to isolate the solid materials, and suspending the solid materials in a carrier.

In some embodiments, digested ECM also can be centrifuged for a second step at about 2000 g to about 3000 g. Thus, the digested ECM can be centrifuged at about 2,500 g to about 3,000 g, such as at about 2,000 g, 2,500 g, 2,750 g or 3,000 g. This centrifugation can occur for about 20 to about 30 minutes, such as for about 20 to about 25 minutes, such as for about 20, about 21, about 22, about 23, about 24, about 25, about 26, about 27, about 28, about 29 or about 30 minutes. The supernatant including the digested ECM is collected.

In additional embodiments, the digested ECM can be centrifuged for a third step at about 10,000 to about 15,000 g. Thus, the digested ECM can be centrifuged at about 10,000 g to about 12,500 g, such as at about 10,000 g, 11,000 g or 12,000 g. This centrifugation can occur for about 25 to about 40 minutes, such as for about 25 to about 30 minutes, for example for about 25, about 26, about 27, about 28, about 29, about 30, about 31, about 32, about 33, about 34, about 35, about 36, about 37, about 38, about 39 or about 40 minutes. The supernatant including the digested ECM is collected.

One, two or all three of these centrifugation steps can be independently utilized. In some embodiments, all three centrifugation steps are utilized. The centrifugation steps can be repeated, such as 2, 3, 4, or 5 times. In one embodiment, all three centrifugation steps are repeated three times.

In some embodiments, the digested ECM is centrifuged at about 500 g for about 10 minutes, centrifuged at about 2,500 g for about 20 minutes, and/or centrifuged at about 10,000 g for about 30 minutes. These step(s), such as all three steps are repeated 2, 3, 4, or 5 times, such as three times. Thus, in one non-limiting example, the digested ECM is centrifuged at about 500 g for about 10 minutes, centrifuged at about 2,500 g for about 20 minutes, and centrifuged at about 10,000 g for about 30 minutes. These three steps are repeated three times. Thus, a fibril-free supernatant is produced.

The fibril-free supernatant is then centrifuged to isolate the MBVs. In some embodiments, the fibril-free supernatant is centrifuged at about 100,000 g to about 150,000 g. Thus, the fibril-free supernatant is centrifuged at about 100,000 g to about 125,000 g, such as at about 100,000 g, about 105,000 g, about 110,000 g, about 115,000 g or about 120,000 g. This centrifugation can occur for about 60 to about 90 minutes, such as about 70 to about 80 minutes, for example for about 60, about 65, about 70, about 75, about 80, about 85 or about 90 minutes. In one non-limiting example, the fiber-free supernatant is centrifuged at about 100,000 g for about 70 minutes. The solid material is collected, which is the MBVs. These MBVs then can be re-suspended in any carrier of interest, such as, but not limited to, a buffer.

In further embodiments the ECM is not digested with an enzyme. In these methods, ECM is suspended in an isotonic saline solution, such as phosphate buffered saline. Salt is then added to the suspension so that the final concentration of the salt is greater than about 0.1 M. The concentration can be, for example, up to about 3 M, for example, about 0.1 M salt to about 3 M, or about 0.1 M to about 2M. The salt can be, for example, about 0.1M, 0.15M, 0.2M, 0.3M, 0.4 M, 0.7 M, 0.6 M, 0.7 M, 0.8M., 0.9M, 1.0 M, 1.1 M, 1.2 M, 1.3 M, 1.4 M, 1.5M, 1.6 M, 1.7 M, 1.8M, 1.9 M, or 2M. In some non-limiting examples, the salt is potassium chloride, sodium chloride or magnesium chloride. In other embodiments, the salt is sodium chloride, magnesium chloride, sodium iodide, sodium thiocyanate, a sodium salt, a lithium salt, a cesium salt or a calcium salt.

In some embodiments, the ECM is suspended in the salt solution for about 10 minutes to about 2 hours, such as about 15 minutes to about 1 hour, about 30 minutes to about 1 hour, or about 45 minutes to about 1 hour. The ECM can be suspended in the salt solution for about 15, 20, 25, 30, 35, 40, 45, 50, 55, 60, 65, 70, 75, 80, 85, 90, 95, 100, 105, 110, 115 or 120 minutes. The ECM can be suspended in the salt solution at temperatures from 4° C. to about 50° C., such as, but not limited to about 4° C. to about 25° C. or about 4° C. to about 37° C. In a specific non-limiting example, the ECM is suspended in the salt solution at about 4° C. In other specific non-limiting examples, the ECM is suspended in the salt solution at about 22° C. or about 25° C. (room temperature). In further non-limiting examples, the ECM is suspended in the salt solution at about 37° C.

In some embodiments, the method includes incubating an extracellular matrix at a salt concentration of greater than about 0.4 M; centrifuging the digested extracellular matrix to remove collagen fibril remnants, and isolating the supernatant; centrifuging the supernatant to isolate the solid materials; and suspending the solid materials in a carrier, thereby isolating MBVs from the extracellular matrix.

Following incubation in the salt solution, the ECM is centrifuged to remove collagen fibrils. In some embodiments, digested ECM also can be centrifuged at about 2000 g to about 5000 g. Thus, the digested ECM can be centrifuged at about 2,500 g to about 4,500 g, such as at about 2,500 g, about 3,000 g, 3,500 g, about 4,000 g, or about 4,500 g. In one specific non-limiting example, the centrifugation is at about 3,500 g. This centrifugation can occur for about 20 to about 40 minutes, such as for about 25 to about 35 minutes, such as for about 20, about 21, about 22, about 23, about 24, about 25, about 26, about 27, about 28, about 29, about 30 minutes, about 31, about 32, about 33 about 34 or about 35 minutes. The supernatant is then collected.

In additional embodiments, the supernatant then can be centrifuged for a third step at about 100,000 to about 150,000 g. Thus, the digested ECM can be centrifuged at about 100,000 g to about 125,000 g, such as at about 100,000 g, 110,000 g or 120,000 g. This centrifugation can occur for about 30 minutes to about 2.5 hour, such as for about 1 hour to about 3 hours, for example for about 30 minutes, about 45 minutes, about 60 minutes, about 90 minutes, or about 120 minutes (2 hours). The solid materials are collected and suspended in a solution, such as buffered saline, thereby isolating the MBVs.

In yet other embodiments, the ECM is suspended in an isotonic buffered salt solution, such as, but not limited to, phosphate buffered saline. Centrifugation or other methods can be used to remove large particles (see below). Ultrafiltration is then utilized to isolate MBVs from the ECM, particles between about 10 nm and about 10,000 nm, such as between about 10 and about 1,000 nm, such as between about 10 nm and about 300 nn.

In specific non-limiting examples, the isotonic buffered saline solution has a total salt concentration of about 0.164 mM, and a pH of about 7.2 to about 7.4. In some embodiments, the isotonic buffered saline solution includes 0.002 M KCl to about 0.164 M KCL, such as about 0.0027 M KCl (the concentration of KCL in phosphate buffered saline). This suspension is then processed by ultracentrifugation.

Following incubation in the isotonic buffered salt solution, the ECM is centrifuged to remove collagen fibrils. In some embodiments, digested ECM also can be centrifuged at about 2000 g to about 5000 g. Thus, the digested ECM can be centrifuged at about 2,500 g to about 4,500 g, such as at about 2,500 g, about 3,000 g, 3,500 g, about 4,000 g, or about 4,500 g. In one specific non-limiting example, the centrifugation is at about 3,500 g. This centrifugation can occur for about 20 to about 40 minutes, such as for about 25 to about 35 minutes, such as for about 20, about 21, about 22, about 23, about 24, about 25, about 26, about 27, about 28, about 29, about 30 minutes, about 31, about 32, about 33 about 34 or about 35 minutes.

Microfiltration and centrifugation can be used and combined to remove large molecular weight materials from the suspension. In one embodiment, large size molecule materials, such as more than 200 nm are removed using microfiltration. In another embodiment, large size materials are removed by the use of centrifugation. In a third embodiment both microfiltration and ultracentrifugation are used to remove large molecular weight materials. Large molecular weight materials are removed from the suspended ECM, such as materials greater than about 10,000 nm, greater than about 1,000 nm, greater than about 500 nm, or greater than about 300 nm. The effluent for microfiltration or the supernatant is then subjected to ultrafiltration. Thus, the effluent, which includes particle of less than about 10,000 nm, less than about 1,000 nm, less than about 500 nm, or less than about 300 nm is collected and utilized. This effluent is then subjected to ultrafiltration with a membrane with a molecular weight cutoff (MWCO) of 3,000 to 100,000. 100,000MWCO was used in the example.

Methods for Increasing Retinal Ganglion Cell Survival

Methods are disclosed herein for increasing retinal ganglion cell survival in a subject in need thereof. The subject can be a veterinary subject or a human. The subject can be a mammal. The subject can be avian or a domestic pet, such as a cat, dog or rabbit. The subject can be a non-human, primate, or livestock, including swine, ruminants, horses, and poultry. The methods include selecting a subject in need of treatment to increase retinal ganglion cell survival, and administering to the subject a therapeutically effective amount of MBVs. The MBVs can be derived from the same or a different species than the subject in need of increased retinal ganglion cell survival.

In some embodiments, the subject has glaucoma. The subject can have open angle glaucoma, closed angle glaucoma, or normotensive glaucoma. The glaucoma can be a primary glaucoma or a secondary glaucoma. Any of these subjects can be selected for treatment. Intraocular pressure (IOP), the fluid pressure within the eye, can be measured in units of millimeters of mercury (mmHg) or kilopascals (kPa). Normal intraocular pressure is typically considered to be between 10 mmHg and 20 mmHg. The average value of intraocular pressure is 15.5 mmHg with fluctuations of about 2.75-3.50 mmHg Elevated intraocular pressure (above 21 mmHg or 2.8 kPa) is the most important and only modifiable risk factor for glaucoma. In some embodiments a subject is selected that has elevated intraocular pressure. In other embodiments a subject is selected who has less than elevated intraocular pressure, but who has evidence of glaucomatous damage. For example, the subject may have cupping of the optic disc and an increased or increasing cup-to-disk ratio (for example greater than 0.3, 0.5 or 0.7). In other embodiments the subject may have a slightly elevated IOP in the presence of glaucomatous optic nerve damage (such as a progression in the cup-to-disc ratio).

Testing for glaucoma can include measurements of the intraocular pressure, such as using tonometry, anterior chamber angle examination or gonioscopy, and examination of the optic nerve to identify damage, change in the cup-to-disc ratio, rim appearance and detection of vascular changes. Visual field testing can be performed. The retinal nerve fiber layer can be assessed with imaging techniques such as optical coherence tomography, scanning laser polarimetry, and/or scanning laser ophthalmoscopy (Heidelberg retinal tomogram). Additional tests include tonometry, ophthalmoscopy, perimetry, gonioscopy, pachymetry, and nerve fiber analysis. These methods can be performed in order to select a subject for treatment according to the methods disclosed herein.

In other embodiments, the subject has retinal ganglion cell degeneration caused by injury. In further embodiments, the subject has retinal ganglion cell degeneration caused by a genetic disorder. In some non-limiting examples, the subject has ppressure-independent glaucomatous optic neuropathy, ischemic optic neuropathy, inflammatory optic neuropathy, compressive optic neuropathy, traumatic optic neuropathy. In other non-limiting examples, the subject has arteritic ischemic optic neuropathy, arteritic ischemic optic neuropathy associated with giant cell arteritis, nonarteritic ischemic optic neuropathy, infiltrative optic neuropathy, infiltrative optic neuropathy associated with sarcoidosis, infectious optic neuropathy, infectious optic neuropathy associated with syphilis, infectious optic neuropathy associated with Lyme disease, infectious optic neuropathy associated with toxoplasmosis, infectious optic neuropathy associated with herpes zoster, optic neuritis from demyelinating disease, posradiation optic neuropathy, acrodermatitis enteropathica, hereditary optic neuropathy, hereditary optic neuropathy associated with dominant optic neuropathy, compressive optic neuropathy, compressive optic neuropathy associated with orbital pseudotumor, compressive optic neuropathy associated with thyroid eye disease, autoimmune optic neuropathy, or autoimmune optic neuropathy associated with Lupus.

The subject can have ocular phototoxicity, specifically photic retinopathy, also called photic maculopathy. In some embodiments, the photic retinopathy is caused by exposure to the sun. In other embodiments, the photic retinopathy is caused by exposure to the artificial light. The subject can be at risk for photic retinopathy, also known as photic maculopathy. For example, the subject can be undergoing laser procedures to the eye, or can be a welder.

The subject can have retinal degeneration resulting from trauma, such as exposure to an explosive device. The subject can have had a retinal laser procedure. In further embodiments, the subject has a disease in which neuronal (i.e., non-photoreceptor) degeneration occurs. These include, but are not limited to, glaucoma, retinal artery occlusions, and retinal vein occlusions.

In some embodiments, administration can be systemic. Exemplary routes of administration include, but are not limited to, intravenous, intraperitoneal, or subcutaneous administration.

In some embodiments, administration can be local to the eye, such as using intravitreal or subretinal administration. Administration can also be to the anterior chamber of the eye. In other embodiments, administration can be to the vitreous of the eye. In some embodiments, administration of the vitreous of the eye is accomplished using intravitreal injection, pumps or implants.

Dosage treatment may be a single dose schedule or a multiple dose schedule to ultimately deliver the amount specified above. The doses can be intermittent. Moreover, the subject may be administered as many doses as appropriate.

Individual doses are typically not less than an amount required to produce a measurable effect on the subject, and may be determined based on the pharmacokinetics and pharmacology for absorption, distribution, metabolism, and excretion ("ADME") of the subject composition or its by-products, and thus based on the disposition of the composition within the subject. This includes consideration of the route of administration as well as dosage amount, which can be adjusted for local and systemic (for example, intravenous) applications. Effective amounts of dose and/or dose regimen can readily be determined empirically from pre-clinical assays, from safety and escalation and dose range trials, individual clinician-patient relationships, as well as in vitro and in vivo assays. Generally, these assays will evaluate the retinal ganglion cells, or expression of a biological component (cytokine, specific inflammatory cell, microglia, etc.) that affects the degeneration of these cells.

A therapeutically effective amount of MBVs can be suspended in a pharmaceutically acceptable carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. Other agents can be added to the compositions, such as preservatives and anti-bacterial agents. These compositions can be administered locally to the eye, such as by intravitreously or subretinally.

Local modes of administration include, by way of example, intraocular, intraorbital, subconjunctival, sub-Tenon's, subretinal or transscleral routes. Administration can also be to the anterior chamber of the eye. In an embodiment, significantly smaller amounts of the components (compared with systemic approaches) may exert an effect when administered locally (for example, intravitreally) compared to when administered systemically (for example, intravenously).

Subretinal injections can be made directly into the macular, e.g., submacular injection. Exemplary methods include intraocular injection (e.g., retrobulbar, subretinal, submacular, intravitreal and intrachoridal), iontophoresis, eye drops, and intraocular implantation (e.g., intravitreal, sub-Tenons and sub-conjunctival).

In some embodiments, a therapeutically effective amount of MBVs is administered by intravitreal injection. A general method for intravitreal injection may be illustrated by the following brief outline. This example is merely meant to illustrate certain features of the method, and is in no way meant to be limiting. Procedures for intravitreal injection are known in the art (see, for example Peyman, et al. (2009) Retina 29(7):875-912 and Fagan and Al-Qureshi, (2013) Clin. Experiment. Ophthalmol. 41(5):500-7). Other methods of intraocular administration are known in the art, and include subretinal administration.

Briefly, a subject for intravitreal injection may be prepared for the procedure by pupillary dilation, sterilization of the eye, and administration of anesthetic. Any suitable mydriatic agent known in the art may be used for pupillary dilation. Adequate pupillary dilation may be confirmed before treatment. Sterilization may be achieved by applying a sterilizing eye treatment, e.g., an iodide-containing solution such as povidone-iodine (BETADINE®). A similar solution may also be used to clean the eyelid, eyelashes, and any other nearby tissues (e.g., skin). Any suitable anesthetic may be used, such as lidocaine or proparacaine, at any suitable concentration. Anesthetic may be administered by any method known in the art, including without limitation topical drops, gels or jellies, and subconjuctival application of anesthetic.

Prior to injection, a sterilized eyelid speculum may be used to clear the eyelashes from the area. The site of the injection may be marked with a syringe. The site of the injection may be chosen based on the lens of the patient. For example, the injection site may be 3-3.5 mm from the limus in pseudophakic or aphakic patients, and 3.5-4 mm from the limbus in phakic patients. The patient may look in a direction opposite the injection site. During injection, the needle can be inserted perpendicular to the sclera and pointed to the center of the eye. The needle can be inserted such that the tip ends in the vitreous, rather than the subretinal space. Any suitable volume known in the art for injection may be used. After injection, the eye can be treated with a sterilizing agent such as an antibiotic. The eye can also be rinsed to remove excess sterilizing agent.

Intravitreal injection (or administration by any other route of administration) of a therapeutically effective amount of MBVs can be performed once, or can be performed repeatedly, such as 1, 2, 3, 4, 5, 6, 7, 8, 9, or 10 times. Administration can be performed biweekly, weekly, every other week, monthly, or every 2, 3, 4, 5, or 6 months.

Pharmaceutical compositions that include a therapeutically effective amount of MBVs can be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated. In some embodiments, the disclosed methods increase the survival of retinal ganglion cells when administered to the eye of a subject.

The subject can be administered additional therapeutic agents, in the same composition or in a different composition. These therapeutic agents include, but are not limited to, an agent that lowers intraocular pressure. The agent can be a) a prostaglandin analog, b) a beta-adrenergic blocker, c) an alpha-adrenergic agonist, or d) a cholinergic agonist. Exemplary agents include latanoprost, bimatorpost, travoprost, timolol, betaxolol, brimonidine, pilocarpine, dorzolamide, brinzolamide, and acetazolamide. In some specific non-limiting examples, the agent is a) latanoprost, b) timolol, c) brimonidine, or d) pilocarpine. The subject can be administered a Rho-kinase inhibitor, such as, but not limited to, ripasudil or netarsudil.

Additional agents that can be administered to the subject include antibacterial and antifungal antibiotics, as well as non-steroidal anti-inflammatory agents to reduce risk of infection and inflammation. Additional agents can be administered by any route. The additional agents can be formulated separately, or in the same composition as the MBVs.

Agents of use include minoglycosides (for example, amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (for example, azidamfenicol, chloramphenicol, florfenicol, thiamphenicol), ansamycins (for example, rifamide, rifampin, rifamycin sv, rifapentine, rifaximin), β-lactams (for example, carbacephems (e.g., loracarbef), carbapenems (for example, biapenem, imipenem, meropenem, panipenem), cephalosporins (for example, cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (for example, cefbuperazone, cefmetazole, cefininox, cefotetan, cefoxitin), monobactams (for example, aztreonam, carumonam, tigemonam), oxacephems, flomoxef, moxalactam), penicillins (for example, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin g benzathine, penicillin g benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, ticarcillin), other (for example, ritipenem), lincosamides (for example, clindamycin, lincomycin), macrolides (for example, azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (for example, amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (for example, apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin). Agents of use also include synthetic antibacterials, such as 2,4-Diaminopyrimidines (for example, brodimoprim, tetroxoprim, trimethoprim), nitrofurans (for example, furaltadone, furazolium chloride, nifuradene, nifuratel, nifurfoline, nifurpirinol, nifurprazine, nifurtoinol, nitrofurantoin), quinolones and analogs (for example, cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (for example, acetyl sulfamethoxypyrazine, benzylsulfamide, chloramine-b, chloramine-t, dichloramine t, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidocchrysoidine, sulfamoxole, sulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (for example, acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (for example, clofoctol, hexedine, methenamine, methenamine anhydromethylene-citrate, methenamine hippurate, methenamine mandelate, methenamine sulfosalicylate, nitroxoline, taurolidine, xibornol).

Additional agents of use include antifungal antibiotics such as polyenes (for example, amphotericin B, candicidin, dennostatin, filipin, fungichromin, hachimycin, hamycin, lucensomycin, mepartricin, natamycin, nystatin, pecilocin, perimycin), others (for example, azaserine, griseofulvin, oligomycins, neomycin undecylenate, pyrrolnitrin, siccanin, tubercidin, viridin) allylamines (for example, butenafine, naftifine, terbinafine), imidazoles (for example, bifonazole, butoconazole, chlordantoin, chlormiidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (for example, tolciclate, tolindate, tolnaftate), triazoles (for example, fluconazole, itraconazole, saperconazole, terconazole) others (for example, acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate). Antineoplastic agents can also be of use including (1) antibiotics and analogs (for example, aclacinomycins, actinomycin, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), (2) antimetabolites such as folic acid analogs (for example, denopterin, edatrexate, methotrexate, piritrexim, pteropterin, trimetrexate), (3) purine analogs (for example, cladribine, fludarabine, 6-mercaptopurine, thiamiprine, thioguanine), (4) pyrimidine analogs (for example, ancitabine, azacitidine, 6-azauridine, carmofur, cytarabine, doxifluridine, emitefur, enocitabine, floxuridine, fluorouracil, gemcitabine, tagafur).

Steroidal anti-inflammatory agents can also be used such as 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, cyclosporine, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

In addition, non-steroidal anti-inflammatory agents can be used. These include aminoarylcarboxylic acid derivatives (for example, enfenamic acid, etofenamate, flufenamic acid, isonixin, meclofenamic acid, mefenamic acid, niflumic acid, talniflumate, terofenamate, tolfenamic acid), arylacetic acid derivatives (for example, aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (for example, bumadizon, butibufen, fenbufen, xenbucin), arylcarboxylic acids (for example, clidanac, ketorolac, tinoridine), arylpropionic acid derivatives (for example, alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (for example, difenamizole, epirizole), pyrazolones (for example, apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (for example, acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (for example, ampiroxicam, droxicam, isoxicam, lornoxicam, piroxicam, tenoxicam), .epsilon.-acetamidocaproic acid, s-adenosylmethionine, 3-amino-4-hydroxybutyric acid, amixetrine, bendazac, benzydamine, .alpha.-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, and zileuton.

Implants are also of use in the methods disclosed herein. The implants can be inserted into the eye by a variety of methods, including placement by forceps or by trocar following making an incision in the sclera (for example, a 2-3 mm incision) or other suitable sites. In some cases, the implant can be placed by trocar without making a separate incision, but instead by forming a hole directly into the eye with the trocar. The method of placement can influence the release kinetics. For example, implanting the device into the vitreous or the posterior chamber with a trocar may result in placement of the device deeper within the vitreous than placement by forceps, which may result in the implant being closer to the edge of the vitreous. The location of the implanted device may influence the concentration gradients of the therapeutic agent surrounding the device, and thus influence the release rates (for example, a device placed closer to the edge of the vitreous may result in a slower release rate, see U.S. Pat. Nos. 5,869,079 and 6,699,493). In one embodiment, an implant is formulated with a bioerodible polymer matrix.

Generally, when implants are used, the MBVs are homogeneously distributed through the polymeric matrix, such that it is distributed evenly enough that no detrimental fluctuations in rate of release occur because of uneven distribution of the immunosuppressive agent in the polymer matrix. The selection of the polymeric composition to be employed varies with the desired release kinetics, the location of the implant, patient tolerance, and the nature of the implant procedure. The polymer can be included as at least about 10 weight percent of the implant. In one example, the polymer is included as at least about 20 weight percent of the implant. In another embodiment, the implant comprises more than one polymer. These factors are described in detail in U.S. Pat. No. 6,699,493. Characteristics of the polymers generally include biodegradability at the site of implantation, compatibility with the agent of interest, ease of encapsulation, and water insolubility, amongst others. Generally, the polymeric matrix is not fully degraded until the drug load has been released. The chemical composition of suitable polymers is known in the art (for example, see U.S. Pat. No. 6,699,493).

Administration may be provided as a single administration, a periodic bolus or as continuous infusion. In some embodiments, administration is from an internal reservoir (for example, from an implant disposed at an intra- or extra-ocular location (see, U.S. Pat. Nos. 5,443,505 and 5,766,242)) or from an external reservoir (for example, from an intravenous bag). Components can be administered by continuous release for a specific period from a sustained release drug delivery device immobilized to an inner wall of the eye or via targeted transscleral controlled release into the choroid (see, for example, PCT/US00/00207, PCT/US02/14279, Ambati et al., Invest. Opthalmol. Vis. Sci. 41:1181-1185, 2000, and Ambati et al., Invest. Opthalmol. Vis. Sci. 41:1186-1191, 2000). A variety of devices suitable for administering components locally to the inside of the eye are known in the art. See, for example, U.S. Pat. Nos. 6,251,090, 6,299,895, 6,416,777, 6,413,540, and PCT Publication No. PCT/US00/28187.

In some embodiments, the method includes the step of detecting that a therapeutic benefit has been achieved. Measures of therapeutic efficacy will be applicable to the particular disease being modified, and will recognize the appropriate detection methods to use to measure therapeutic efficacy. The subject can be evaluated for response using any methods known in the art. These include, but are not limited to, ophthalomosccopy, perimetry, gonioscopy, pachymetry, or nerve fiber analysis. In some embodiments, retinal ganglion cell number and/or viability can be assessed. One of skill in the art can readily determine that the disclosed methods are effective. For example it can be determined by whether the cup-to-disc ratio has stabilized. Scanning laser polarimetry or optical coherence tomography could be used, for example to perform retinal nerve fiber layer analysis. A visual field test could be used to monitor progression of glaucoma. For any of the disclosed methods, therapeutic efficacy in treating a vision deficiency can as an alteration in the individual's vision.

Therapeutic efficacy can also be assessed by measuring cytokine produced by microglia and/or astrocytes. In some embodiments, cytokine is IL-1$\beta$, IL-6, or TNF-$\alpha$. Methods for measuring cytokines are known in the art, and include, without limitation, bioassays, radioimmunoassay (RIA) and enzyme linked immunosorbent assays (ELISA). Exemplary methods are disclosed below.

EXAMPLES

Diffusion tensor MRI, complimented with optokinetics and manganese enhanced MRI, can detect small changes in axon degeneration rates longitudinally that correlate with changes in visual behavior. It is disclosed herein that ECM scaffolds can alter the default healing response in the adult rat central nervous system (CNS) by decreasing astrocyte and microglial activation and increasing retinal ganglion cell (RGC) survival and RGC developmental gene expression.

Although ECM has been shown to modulate the default healing response in tissues such as the esophagus, the mechanisms and bioactive factors responsible for the effects are not fully elucidated. MBVs elicit cellular responses in vitro similar to the parent ECM, from which they are derived, suggesting that MBVs are critical bioactive factors within ECM that regulate cellular responses. Additionally, MBVs are enriched in miRNAs known to regulate cellular survival and growth, and have Lox on their surface.

Therapies are disclosed herein that modulate the default healing response to preserve or to restore neurologic function. It is disclosed that tissue-specific ECMs, specifically MBVs isolated from ECMs, differentially regulate RGC survival, axon growth, and tissue remodeling. MBVs are shown to promote RGC survival and axon regeneration and decrease the innate immune response in the optic nerve after acute optic nerve ischemia.

Example 1

Materials and Methods

Animals: Sprague-Dawley rats were provided by Charles River Laboratories (Wilmington, Mass.). Animals care and protocols complied with guidelines from the Guide for the Care and Use of Laboratory Animals published by the National Institutes of Health.

Urinary bladder extracellular matrix decellularization and hydrogel formation: Porcine urinary bladders from adult market weight pigs were provided by a local abattoir. Urinary bladders were decellularized as described (Faust et al., J Biomater Appl, 2017. 31(9): p. 1277-1295). Decellularization was confirmed using established methods to quantify DNA, including H&E staining and visualization through gel electrophoresis (Faust et al., J Biomater Appl, 2017. 31(9): p. 1277-1295); Freytes et al., Biomaterials, 2008. 29(11): p. 1630-7; Rosario et al., Regen Med, 2008. 3(2): p. 145-56). Decellularized urinary bladder extracellular matrix (UBM-ECM) was frozen, lyophilized, and stored at $-20°$ C. until use. UBM-ECM hydrogels at 10 mg/ml were made as previously described (Faust et al., J Biomater Appl, 2017. 31(9): p. 1277-1295; Medberry et al., Biomaterials, 2013. 34(4): p. 1033-40). Briefly, lyophilized UBM-ECM was milled to a powder, digested at 10 mg/ml with 1 mg/ml pepsin for 48 hours (hrs), and the pH adjusted to 7.4.

Matrix bound nanovesicle (MBV) isolation: Lyophilized UBM-ECM was digested with Liberase TL (5401020001, Sigma-Aldrich) in Tris buffer (50 mM Tris pH7.5, 5 mM $CaCl_2$, 150 mM NaCl) for 24 hrs at room temperature (RT) on an orbital rocker. Digested UBM-ECM was centrifuged at (10,000 g, 30 mins). The MBV were pelleted by ultracentrifugation (100,000 g, Beckman Coulter Optima L-90K Ultracentrifuge) at $4°$ C. for 2 hrs and further purified by size exclusion chromatography, using a Sepharose CL-2B resin. Purified MBV were stored at $-80°$ C. until use. All MBV isolations were analyzed morphologically by transmission electron microscopy (TEM) as described (Huleihelet al., Adv, 2016. 2(6): p. e1600502). MBV on TEM grids were observed at 80 kV with a JEOL 1210 transmission electron microscope equipped with a high-resolution AMT digital camera.

Retinal ganglion cell (RGC) isolation: RGCs were isolated from postnatal day three Sprague-Dawley rat pups as described (Barres et al., Neuron, 1988. 1(9): p. 791-803). Purified RGCs were seeded in neurobasal-SATO (nb-SATO) media at 3,000 RGCs per well in 96-well culture plates (087723B, Falcon) coated with poly-D-lysine for 1 hr at RT (70 kDa, 10 µg/ml, Sigma-Aldrich Corp., St. Louis, Mo., USA) and laminin overnight ($37°$ C., 2 µg/ml, Sigma-Aldrich Corp.). MBV were resuspended in sterile PBS and added to RGC cultures in triplicate wells at concentrations ranging from 5-80 µg/ml. UBM-ECM hydrogel (250 µg/ml) and nb-SATO media were used as controls. RGCs were cultured at $37°$ C., 10% $CO_2$ for 3 days.

RGC viability: RGC viability was analyzed using a calcein and propidium iodide live/dead kit per the manufacturer's instructions (Life Technologies, R37601). Briefly, the calcein and propidium iodide were mixed and incubated with the RGCs for 15 mins at RT. Five random non-overlapping fields were imaged per well at 20× using epi-fluorescence fluorescein and rhodamine filter sets (Zeiss, Axio Observer). Live and dead RGCs were quantified using ImageJ (National Institutes of Health, Bethesda, Md., USA). Data represent triplicates from three independent experimental repeats totaling at least 45 fields of view.

RGC neurite growth quantification: Neurite growth was analyzed as described (Steketee, et al., Invest Ophthalmol Vis Sci, 2014. 55(7): p. 4369-77; Van der Merwe, et al., EBioMedicine, 2017. 26: p 47-59). Briefly, RGCs were fixed with 4% paraformaldehyde (Alfa Aesar, 30525-89-4) in PBS for 15 minutes (min) and then washed with PBS (3×). RGCs were permeabilized with 0.2% Triton X-100 in PBS for 15 mins, blocked with 1% BSA (Fisher Scientific) in PBS for 15 mins, and incubated overnight at 4° C. with anti-β III tubulin (1:300, TUJ-1, Millipore) in PBS. After incubation, RGCs were washed with PBS (3×), incubated in FITC-rabbit anti-chicken IgY H+L (1:150, Thermo Scientific) for 3 hrs at RT, washed with PBS (3×), and stained with DAPI (1:3000, Invitrogen) for 15 mins at RT. RGCs were washed with PBS (3×) and imaged at 20× (Zeiss, Axio Observer). For each well, total neurite growth was measured for the first ten RGCs randomly encountered that were not contacting another RGC using the ImageJ plugin NeuronJ. Data represent total RGC neurite growth from triplicate wells in three experimental repeats, totaling at least 90 neurons per group.

Microglia cultures: Primary rat microglia (Lonza, R-G-535) were plated at 50,000 cells per well in 96-well plates per the supplier's recommendation. For all experiments, microglia were initially incubated for 24 hrs at 37° C., 5% $CO_2$ to facilitate adherence. After 24 hrs, the supernatants were removed and replaced with fresh microglia media.

For unprimed microglia cultures, the following reagents were added to triplicate wells: microglia media only, lipopolysaccharide (LPS, 100 ng/ml) and interferon gamma (IFNγ, 20 ng/ml), interleukin-4 (IL-4, 20 ng/ml), UBM-ECM hydrogel (250 µg/ml), or MBV (5 µg/ml). After 24 hours, media was collected for ELISA analysis or to treat astrocytes.

For primed microglial cultures, microglia were treated with LPS (100 ng/ml) and IFNγ (20 ng/ml) for 6 hrs, supernatants removed, microglia rinsed with microglia media, and treated with the following in triplicate wells for an additional 24 hrs: microglia media, UBM-ECM (250 µg/ml), or MBV (5 µg/ml). After the additional 24 hrs incubation, supernatants were collected for ELISA assays or to treat astrocytes.

Astrocyte cultures: Primary rat astrocytes (ScienCell Research Laboratories, R1800) were plated at 5,000 cells per well in a 96-well plate per the supplier's instructions. Astrocytes were allowed to adhere for 24 hrs at 37° C., 5% $CO_2$. To determine the effect that microglia polarization has on astrocytes, microglia conditioned media (groups and collection described in "Microglia cultures" section) was added to triplicate astrocyte wells and incubated for 24 hrs. After initial 24 hr incubation with microglia conditioned media, astrocytes were rinsed with astrocyte media, incubated with fresh astrocyte media for an additional 24 hrs, and supernatants collected for ELISA assays. To determine the effect of astrocyte supernatants on RGC viability, a transwell plate was used. Astrocytes were plated on the transwell insert at 5,000 cells per insert per the supplier's instructions, and the bottom chamber filled with astrocyte media. Astrocytes were allowed to adhere for 24 hrs at 37° C., 5% $CO_2$. After initial 24 hr incubation, microglia conditioned media was added in triplicate to astrocytes in the insert and incubated for 24 hrs. After 24 hrs, the astrocytes were rinsed, and media replaced with fresh nb-SATO media for an additional 24 hrs. After incubation, the nb-SATO media in the bottom wells were collected for RGC cultures.

ELISA analysis: Microglia and astrocyte supernatants were analyzed IL-1β (R&D Systems, DY501), IL-6 (R&D Systems, DY506), and TNF-α (BioLegend, Cat. #438204) expression according to manufacturer's instructions. Duplicate samples were analyzed from three independent experimental repeats.

Retinal ganglion cell responses to astrocyte conditioned media: RGCs were isolated and plated as described above and allowed to adhere for 24 hrs at 37° C., 10% $CO_2$. To determine the effects of astrocyte conditioned media on RGC survival, supernatants from astrocytes were collected as described and added to RGC wells in triplicate and incubated for 72 hrs at 37° C., 10% $CO_2$. RGC viability from three independent experiments was analyzed as described in the RGC viability section above.

In vivo MBV dose response: RGC survival was tested with three doses of MBV in vivo: 5, 10, and 20 µg/ml (n=5 animals per group). Animals were anesthetized via isoflurane inhalation (3% induction, 1.5% maintenance). One drop proparacaine hydrochloride ophthalmic solution (Bausch & Lomb, Inc., Rochester, N.Y.) and one drop tropicamide ophthalmic solution (Akorn, Lake Forest, Ill.) were topically applied to both eyes of twenty animals to induce analgesia and pupil dilation, respectively. An 18 g needle was used to make a small hole in the sclera immediately posterior to the limbus. Under a surgical microscope, a Hamilton micro-syringe was inserted into the vitreous through the scleral opening. The needle tip was placed as close as possible to the optic nerve head, and care was taken not to touch the retina or lens. MBV were diluted in sterile PBS to the appropriate concentrations. All injection volumes were 1 and sterile PBS was used as vehicle control (n=5 per group). 1 µl MBV or PBS were injected into the vitreous and the needle was held in place for 30 secs to allow the MBV or PBS to diffuse into the vitreous. The needle was removed and one drop gentamicin antibiotic ointment (Akorn, Lake Forest, Ill.) was applied topically immediately after removal of the needle. The animals received two additional injections at days 2 and 7 using the same techniques described. Animals were sacrificed 14 days after MBV injection and retinas removed for RGC quantification.

Intraocular pressure elevation with MBV treatment: Acute intraocular pressure (IOP) elevation was induced as previously described. Forty-five animals received IOP elevation in the right eye only via saline anterior chamber perfusion and the left eyes served as uninjured control. Animals were anesthetized with an intraperitoneal injection of a 75:10 mg/kg ketamine/xylazine cocktail, and anesthesia was confirmed with a toe pinch reflex. One drop each of proparacaine and tropicamide were applied to the right eyes to induce analgesia and pupil dilation, respectively. A 30 g needle was connected to a sterile saline reservoir (0.9% sodium chloride; Baxter International Inc., Deerfield, Ill.) and the needle tip inserted into the anterior chamber. The needle was inserted parallel to the iris using a surgical microscope and secured in place. The saline reservoir was elevated to increase the IOP from 15 mmHg to 130 mmHg and secured in place for 60 mins. The IOP was measured using a pressure transducer (BIOPAC Systems, Goleta, Calif., USA) and a handheld tonometer. After 60 mins, the saline reservoir was lowered, and the needle removed from the anterior chamber. One drop gentamicin was applied to the eye immediately after removing the needle. Fifteen animals (n=10 for histology, n=5 for ERG) received 1 µl 5 µg/ml MBV treatment immediately after IOP elevation, and at days 2 and 7 after IOP elevation, using the injection technique described in the previous section. Fifteen animals (n=10 for histology, n=5 for ERG) were used for vehicle controls and received 1 µl of PBS injected intravitreally immediately after IOP elevation and at days 2 and 7 after IOP elevation. Fifteen animals (n=10 for histology, n=5 for ERG) received IOP elevation without any injections.

Cholera toxin subunit B injection: Five animals per group received cholera toxin subunit B (CtxB) injections on day 11, three days prior to sacrifice on day 14. Cholera toxin subunit B (recombinant), Alexa Fluor 594 Conjugate (LifeTech, Cat #C3477) was resuspended in sterile PBS to yield a 1% solution. Animals were anesthetized via isoflurane inhalation (3% induction, 1.5% maintenance). Intravitreal injection technique was used as described in the previous section, and 2 µl of the 1% CtxB solution was injected into the vitreous. The Hamilton syringe needle was held in place for 30 secs before removal, and one drop gentamicin applied topically after removing the needle from the eye.

Immunohistochemistry: Ten animals per group were used for immunohistochemistry. Animals were sacrificed, and the retinas and optic nerves removed and fixed in 4% paraformaldehyde in PBS for 30 mins. Retinas and optic nerves were rinsed three times in PBS for 5 mins each. Retinas were quartered and permeabilized/blocked in IHC blocking buffer (3% Triton X-100, 0.5% Tween-20, 1% BSA, and 0.1% sodium azide in PBS) for 2 hrs at RT on a shaker at 60 RPM. Retinas from animals that received CtxB injections were labeled with 1:250 anti-CtxB (Mouse anti-CtxB, Abcam, AB62429) in IHC blocking buffer, and remaining retinas were co-labeled with 1:250 anti-RNA-binding protein with multiple splicing (Rabbit anti-RBPMS, Phosphosolutions, 1830-RBPMS) and 1:250 anti-Brn3A (Mouse anti-Brn3A, Santa Cruz, SC-8429) in IHC blocking buffer for 48 hrs at 4° C. on a shaker at 60 RPM. Retinas were rinsed three times with 0.3% Tween-20 in PBS and incubated in 1:500 Alexa Fluor 488 donkey anti-rabbit (Abcam, AB150073) and Alexa Fluor 555 goat anti-mouse (Abcam, AB150114) in IHC blocking buffer for 24 hrs at 4° C. on a shaker at 60 RPM. Retinas were rinsed three times with 0.3% Tween-20 in PBS, mounted on glass microscope slides, coverslipped with Vectashield (Vector Laboratories, H-1200), and imaged with epi-fluorescence (Zeiss, Axio Observer). Similar to previous quantification methods (Shaw, et al., Exp Eye Res, 2017. 158: p. 33-42) retinas were quartered prior to staining and three images were taken at the periphery and the center retina (around the optic nerve head) on each quarter section, thereby totaling 12 images at the periphery and 12 images at the center per retina. Previous studies showed IOP elevation causes higher RGC cell death at the periphery of the retina (Chen et al., Invest Ophthalmol Vis Sci, 2011. 52(1): p. 36-44), therefore RGC survival was analyzed at two locations.

Optic nerves were embedded in paraffin and sectioned on a cryostat in 15 µm sections. Sections were blocked/permeabilized in IHC blocking buffer for 2 hrs at RT and rinsed twice with 0.3% Tween-20 in PBS. Sections were labeled with 1:500 anti-GAP43 (Rabbit anti-GAP-43, Abcam, AB16053), 1:500 anti-GFAP (Rabbit anti-GFAP, 1:500, Abcam, AB7260), or 1:250 anti-CtxB (Mouse anti-CtxB, Abcam, AB62429) for 24 hrs at 4° C. The sections were rinsed three times with 0.3% Tween-20 in PBS and incubated in 1:500 Alexa Fluor 488 donkey anti-rabbit (Abcam, AB150073) or Alexa Fluor 555 goat anti-mouse (Abcam, AB150114) in IHC blocking buffer for 24 hrs at 4° C. Sections were rinsed twice with 0.3% Tween-20 in PBS and incubated with 4 µg/ml Hoechst stain (Sigma-Aldrich, H6024) in IHC blocking buffer for 15 mins at RT. The sections were rinsed three times with 0.3% Tween-20 in PBS, mounted on a cover slip with Vectashield, and imaged with epi-fluorescence (Zeiss, Axio Observer). The signal intensities were measured with ImageJ as previously described (Van der Merwe, et al., EBioMedicine, 2017. 26: p 47-59; McCloy et al., Cell Cycle, 2014. 13(9): p. 1400-12). Fifteen regions of interest (ROIs) were drawn evenly distributed along the optic nerve and four ROIs were drawn on the image background. The area, mean fluorescence and integrated density was measured for each image and the signal intensity calculated based on the following equation: CTCF=integrated density−(area×mean background fluorescence).

Electroretinography (ERG): ERG functional analysis was done according to an established protocol (Alarcon-Martinez et al., Mol Vis, 2009. 15: p. 2373-83). In brief, animals were anesthetized with an intraperitoneal injection of a 75:10 mg/kg ketamine/xylazine cocktail, and anesthesia was confirmed with a toe pinch reflex. One drop each of proparacaine and tropicamide were applied to each eye to induce analgesia and pupil dilation, respectively, and eyes were kept lubricated with Goniovisc 2.5% (Sigma Pharmaceuticals, Item #9050) during recordings. Two gold loop electrodes were placed on the cornea, the reference electrode was inserted into the inside of the cheek, and the ground lead electrode was inserted into the quadricep. Bilateral ERG recordings were done simultaneously from both eyes during the trials using a color-light dome. In general, one step of a fixed intensity light was illuminated for 1 ms and the ERG response recorded as a sweep over multiple steps of increasing illumination. Fifty ERG responses were recorded per trial, and a total of three trials were done per light intensity step. The data were analyzed by measuring the Photopic Negative Response (PhNR) and the implicit time of the different waves recorded.

Statistical analysis: All analysis and measurements were done by blinded individuals. One-way analysis of variance (ANOVA) and post-hoc Tukey's test was used to determine significant differences between groups with $p<0.05$. Graphs represent the mean with error bars indicating standard error of the mean (SEM) unless otherwise noted.

Example 2

MBVs are Non-Cytotoxic to RGC and Increase RGC Neurite Growth In Vitro

Figure 1B:
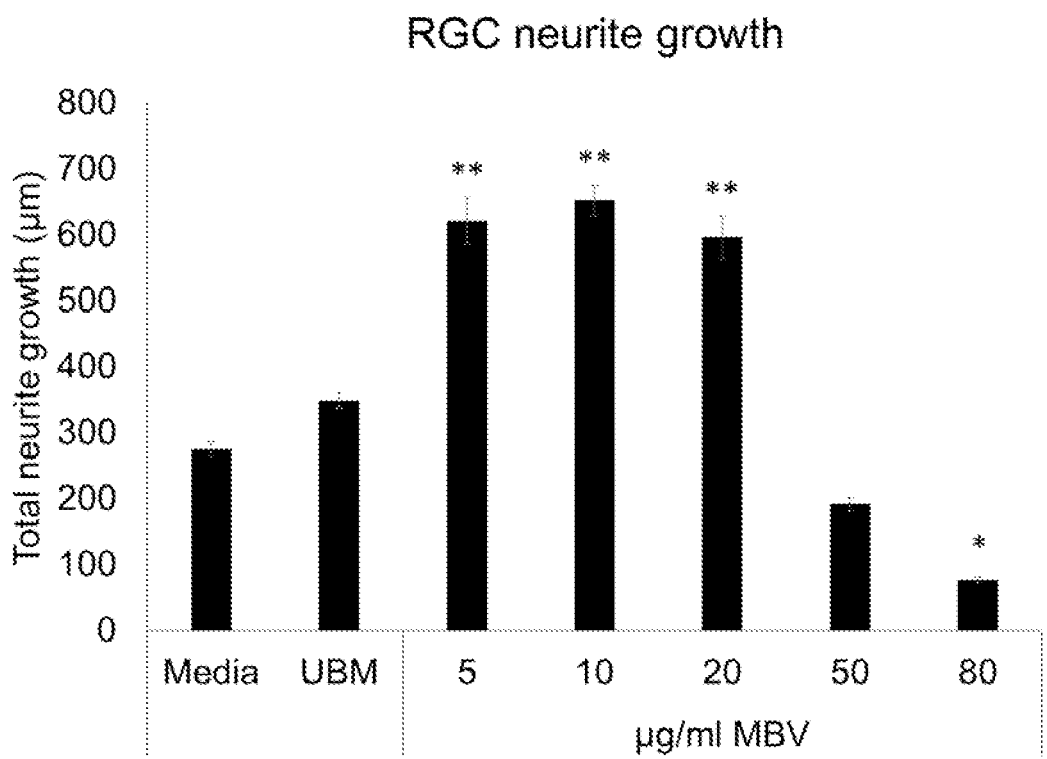

Consistent with previous studies investigating the effects of MBVs on primary neuronal cultures (Faust, et al., J Biomater Appl, 2017. 31(9): p. 1277-12950 in vitro studies suggested MBV derived from UBM-ECM are non-cytotoxic and increase RGC neurite growth compared to media and UBM-ECM hydrogels (FIG. 1). After 3 days of treatment, there was no difference in RGC survival between groups treated with any of the five MBV concentrations, UBM-ECM, or media, indicating UBM-ECM and MBV are non-cytotoxic at the concentrations tested (FIG. 1A). In contrast to RGC viability studies, MBV increased RGC neurite length after 3 days (FIG. 1B). 5, 10, or 20 µg/ml MBV significantly increased RGC neurite growth to 621.5±35.2 µm, 652.4±23.2 µm, and 596.0±32.3 µm, respectively, compared to media (275.2±11.6 µm) and UBM-ECM (348.3±12.1 µm) controls. 50 and 80 µg/ml MBV did not increase RGC neurite growth at 191.6±9.9 µm and 76.4±4.3 µm, respectively.

Example 3

MBVs Suppress Pro-Inflammatory Cytokine Secretion from Microglia and Astrocytes

Figure 2A:
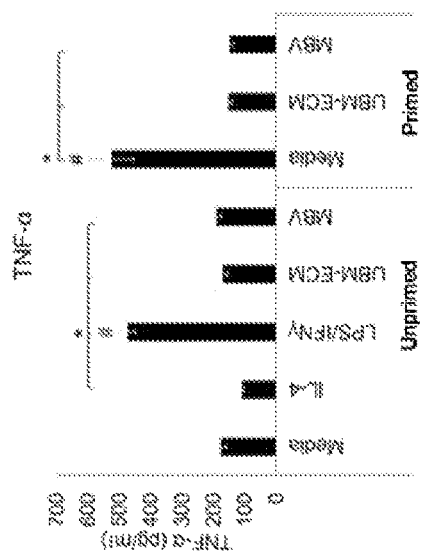
Figure 2B:
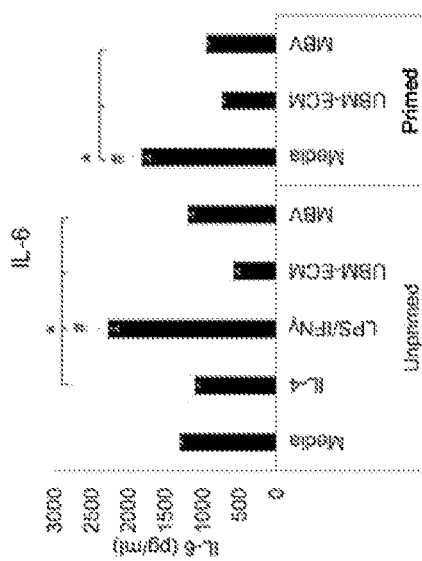
Figure 2C:
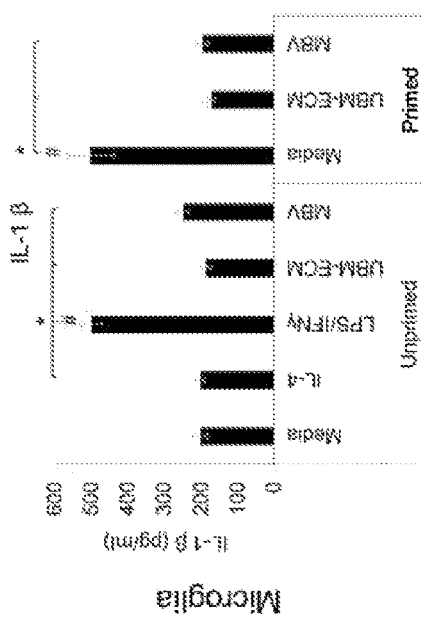

In vitro studies showed MBV suppress pro-inflammatory cytokine secretion from microglia and astrocytes (FIG. 2). Primary microglia were primed with LPS/IFNγ to induce a pro-inflammatory M1-like phenotype, and subsequently treated with media (control), UBM-ECM, or MBV isolated from UBM-ECM to determine whether UBM-ECM and MBV can suppress pro-inflammatory cytokine secretion (FIGS. 2A, 2B, 2C, 2G). Microglia treated with LPS/IFNγ for 24 hrs (unprimed) had increased release of IL-1β, IL-6, and TNF-α in the secretome. Analysis of the secretome of microglia primed with LPS/IFNγ for 6 hrs and then treated with media resulted in a comparable increased release IL-1β, IL-6, and TNF-α, indicating the microglia continued to release pro-inflammatory cytokines after the supernatant was removed and replaced with media. Finally, microglia primed with LPS/IFNγ for 6 hrs and treated with UBM-ECM or MBV showed IL-1β, IL-6, and TNF-α expression levels similar to microglia only treated with media for 24 hrs, indicating the UBM-ECM and MBV treatment for 24 hrs after LPS/IFNγ priming suppresses the release of pro-inflammatory cytokines. Analysis of the astrocyte secretome showed comparable results and trends as the microglia results (FIGS. 2D, 2E, 2F, 2H). Astrocytes treated with supernatants from unprimed microglia treated with LPS/IFNγ showed increased expression of IL-1β, IL-6, and TNF-α, indicating the secretome from pro-inflammatory microglia upregulate the release of pro-inflammatory markers from astrocytes. The secretome from LPS/IFNγ primed microglia treated with media induced a similar upregulated expression of IL-1β, IL-6, and TNF-α from astrocytes, while the secretome from microglia primed with LPS/IFNγ and treated with UBM-ECM or MBV did not increase the expression of pro-inflammatory markers by astrocytes. These results indicate UBM-ECM and MBV treatment following microglia priming can down regulate microglia pro-inflammatory cytokine secretion and prevent secretion of pro-inflammatory cytokines by astrocytes.

Example 4

Figure 3:
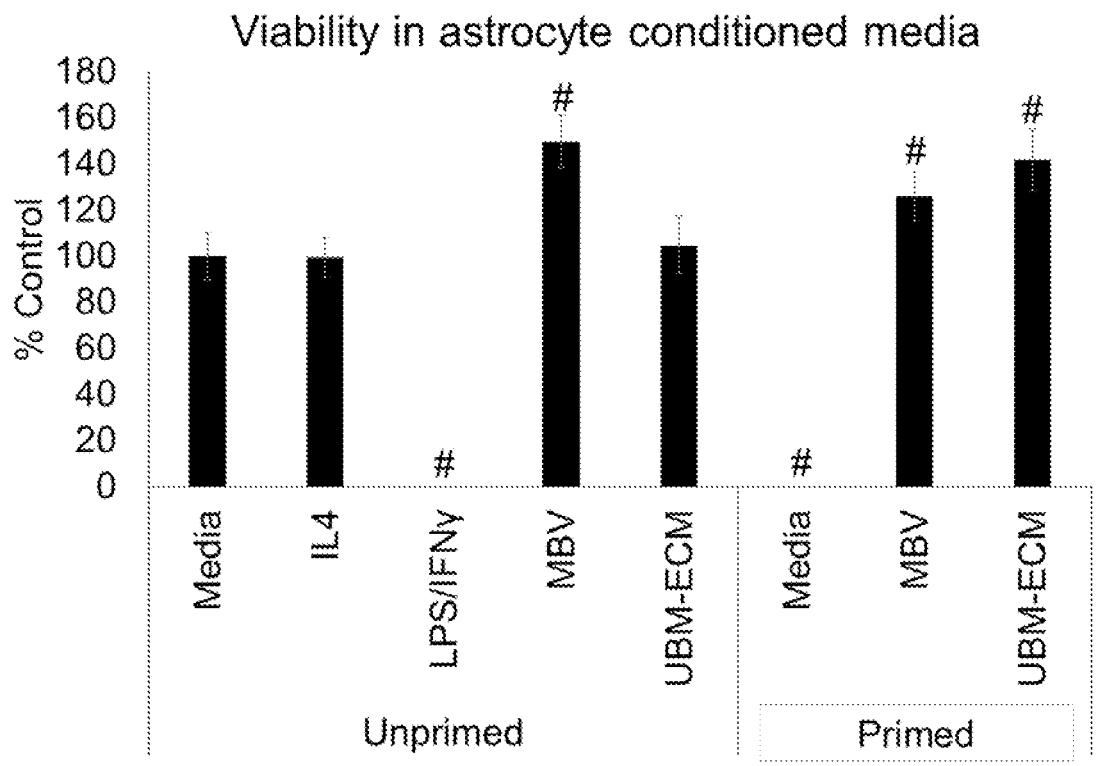
FIG. 3. MBV increase RGC survival in conditioned media from pro-inflammatory astrocytes. RGCs were treated with media from astrocytes cultured with supernatants conditioned by either primed or unprimed microglia. After 3 days, RGCs treated with LPS/IFNγ-unprimed and media-primed media showed 100% RGC death. RGCs treated with primed-MBV or primed-UBM-ECM media showed increased survival. Data normalized to unconditioned media. Error bars represent SEM, experiments represent n>300 neurons analyzed from 3 independent experiments. #p<0.01 compared to unconditioned media.

MBVs Suppress Pro-Inflammatory Cytokine Secretion which Increases RGC Survival In Vitro RGC were treated with astrocyte supernatants, and results showed treating microglia with LPS/IFNγ, or priming with LPS/IFNγ, and subsequent treatment with media resulted in 100% RGC cell death, while UBM-ECM or MBV treatment after microglia priming increased RGC viability and prevented RGC cell death (FIG. 3). These results correspond with previous studies showing microglia M1-like polarization affects RGC viability via astrocyte A1-like polarization (Liddelow et al., Nature, 2017. 541(7638): p. 481-487), and suggest that promoting an anti-inflammatory microglia phenotype over a pro-inflammatory phenotype will increase RGC survival after injury.

Example 5

MBVs are Non-Cytotoxic at Low Concentrations In Vivo

Figure 4:
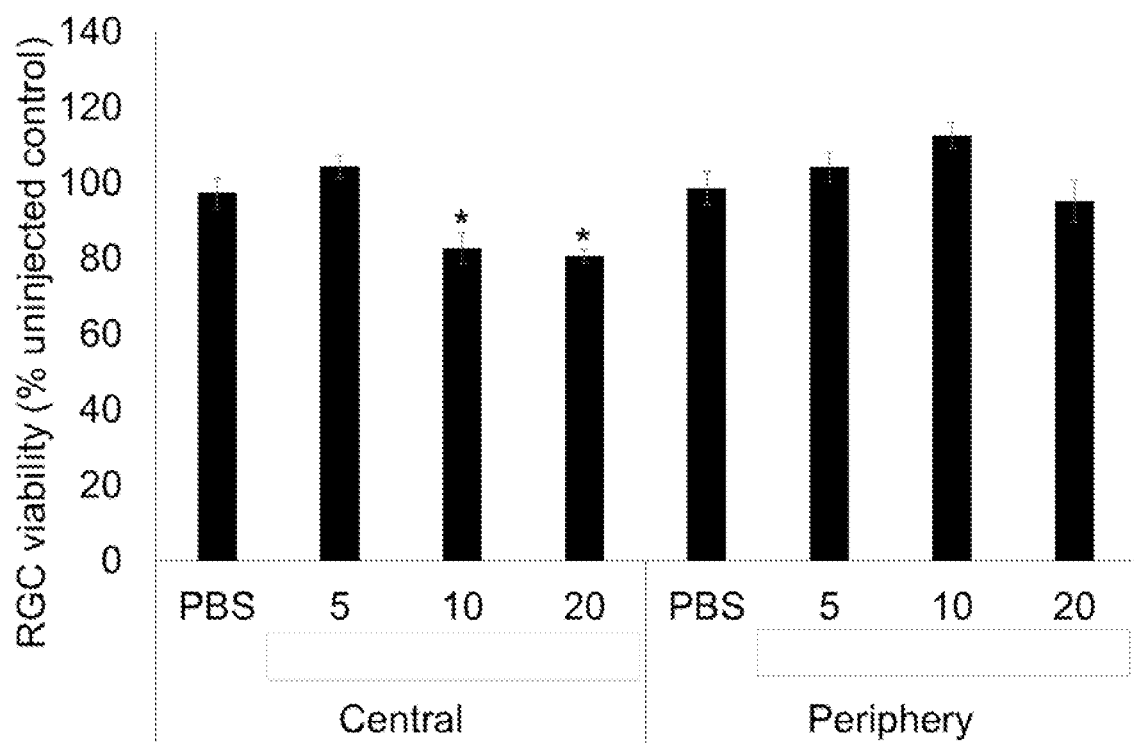
FIG. 4. MBV toxicity in-vivo. MBV were injected intravitreally at 5, 10, and 20 ug/ml, on days 0, 2, and 7 into healthy, uninjured rat eyes. Compared to uninjected controls, RGC viability was unaffected by either PBS or MBV at 5 ug/ml, whereas RGC viability was reduced by MBV at 10 and 20 ug/ml in the central but not the peripheral retina. N=5 animals per group, 12 locations analyzed per retina. *p<0.05 compared to uninjected control. The data show that an MBV concentration of 5 ug/ml can be used without affecting RGC viability in either the central or peripheral retina in vivo.

In-vivo studies were conducted to determine which concentrations of MBV are non-cytotoxic after intravitreal injection. RGC viability was quantified around the optic nerve head (Central) and around the periphery of the retina (Periphery) and results shown as percentage viable RGC as compared to uninjected control (FIG. 4). RGC viability around the periphery was unchanged after MBV and PBS injections compared to uninjected control. RGC viability in the central region was decreased to 82.8±1.9% and 80.7±4.4% of the uninjected control eyes following the injection of 10 µg/ml and 20 µg/ml, respectively, while injection of 5 µg/ml MBV (104.4±4.1%) and PBS (97.4±3.0%) had no effect on RGC viability. The 5 µg/ml MBV concentration was therefore chosen for IOP elevation in vivo experiments.

Example 6

MBVs Increase RGC Survival After IOP Elevation

Figure 5A:
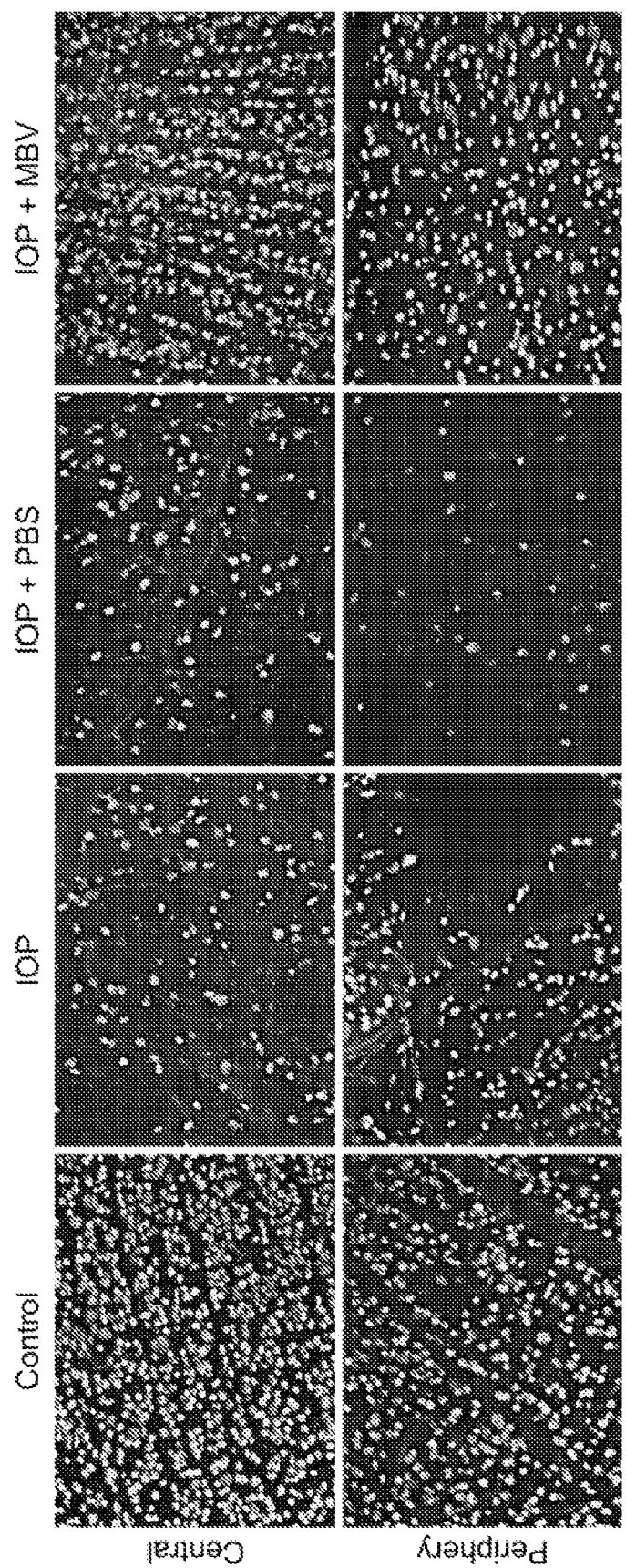
FIGS. 5A-5C. MBV promote increased RGC survival after IOP injury. (A) Representative images showing RGC cell bodies co-labeled with RBPMS and Brn3A in the central and peripheral retina in uninjured control eyes (Control), after untreated IOP elevation (IOP), PBS treated IOP elevation, and MBV treated (IOP+MBV). (B-C) Compared to untreated and PBS treated eyes, quantitative analysis showed MBV increased RGC viability in both the central (B) and in the peripheral retina (C). Error bars represent the SEM, n=5 animals per group, 12 retinal images per retina, totaling 60 images per group. Significance was determined by one-way ANOVA with Post-hoc Tukey's test between groups; #p<0.05, ##p<0.01 compared to media; *p<0.05 between groups FIGS. 6A-6C. MBV suppress RGC axon degeneration. (A) Representative images showing RGC axons labeled with CtxB in the central and peripheral retina in uninjured control eyes (Control), untreated IOP eyes (IOP), PBS treated IOP eyes, and MBV treated IOP eyes. (B) Representative images showing RGC axons labeled with CtxB in the optic nerve of uninjured control eyes (control), untreated IOP eyes (IOP), PBS treated IOP eyes, and MBV treated IOP eyes. (C) Quantitative analysis of CtxB expression showed MBV reduced RGC axon loss. Error bars represent the SEM, n=5 animals per groups and 15 images per optic nerve, totaling 75 images per group. Significance was determined by one-way ANOVA with Post-hoc Tukey's test between groups; #p<0.05, ##p<0.01 compared to media; *p<0.05 between groups.
Figure 5B:
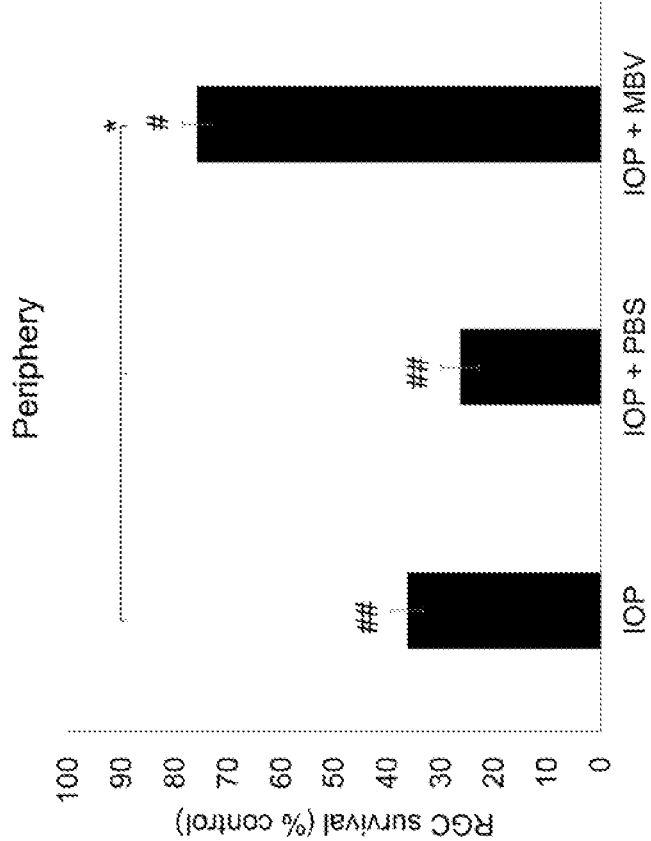
Figure 5C:
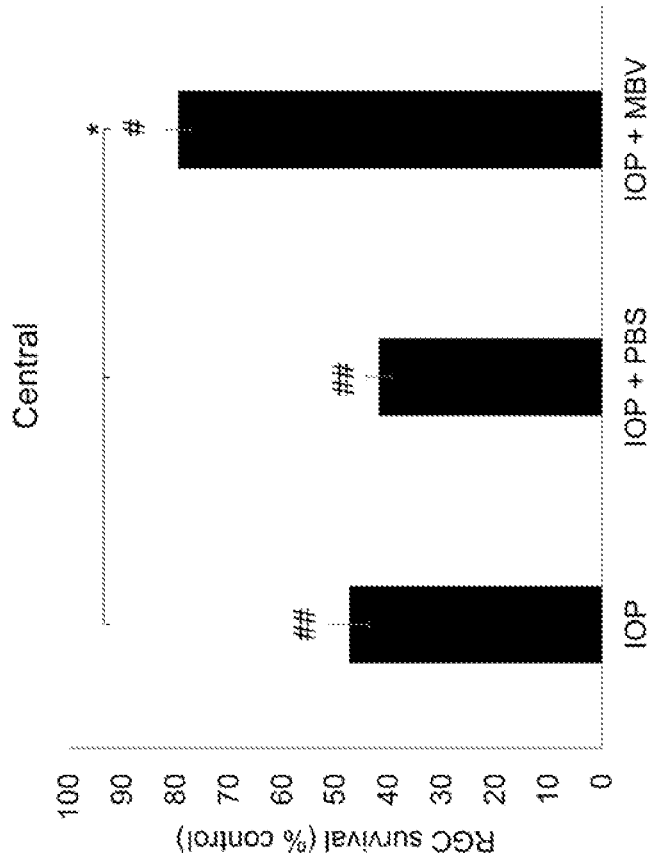

Following IOP elevation, 5 µg/ml MBV were injected intravitreally immediately after IOP elevation, and at days 2 and 7 and resulted in a significant increase in RGC viability (FIG. 5). RGC viability was analyzed 14 days after IOP elevation, and IOP elevation only and IOP elevation with PBS injection resulted in significantly decreased RGC viability in the central retina with 47.4±2.3% and 41.8±2.3% RGC survival compared to uninjured control. MBV treatment caused significant increase in RGC survival in the central retina compared to the two untreated groups, with 79.5±3.8% survival. Similarly, in the peripheral retina, IOP elevation only and IOP elevation with PBS caused a significant decrease in RGC viability at 36.3±3.6% and 26.4±2.8% RGC survival, respectively, compared to uninjured controls. MBV treatment significantly increased RGC survival to 75.9±4.2% compared to uninjured controls.

Example 7

MBVs Increase RGC Axon Survival After IOP Elevation

Figure 6A:
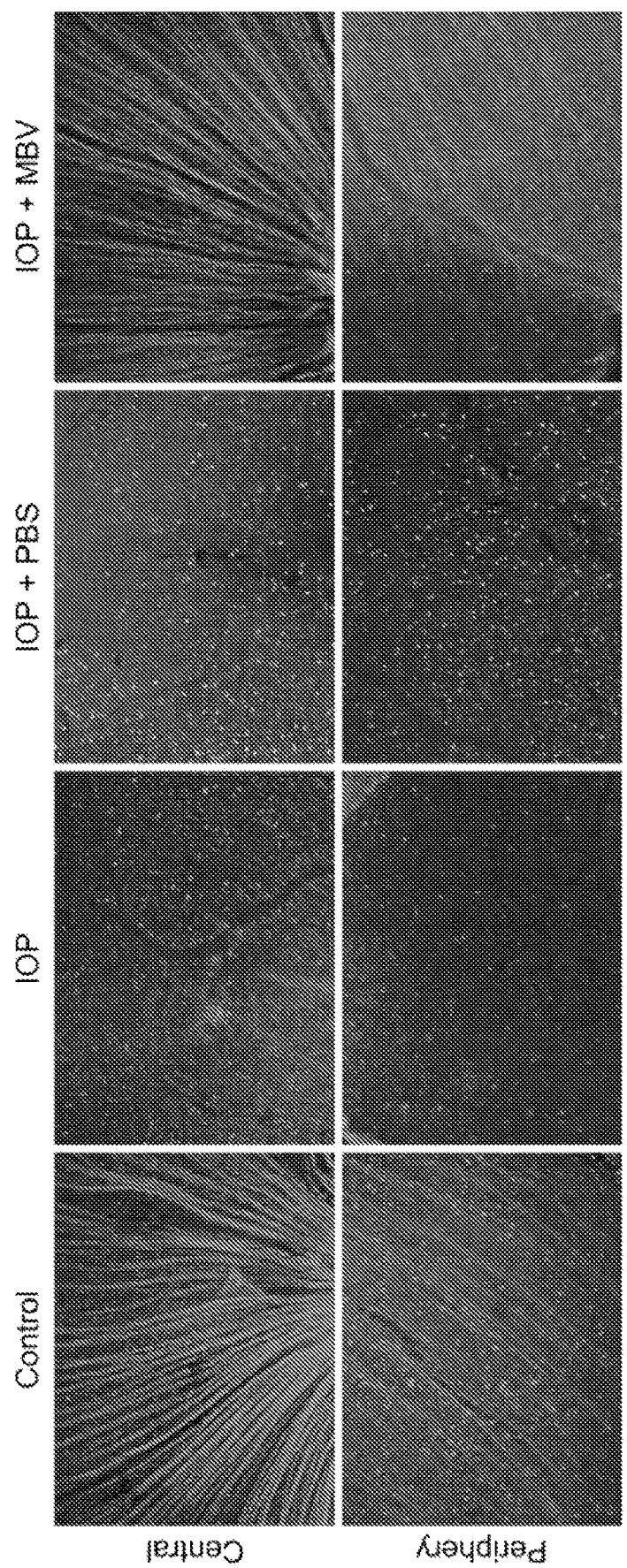
Figure 6C:
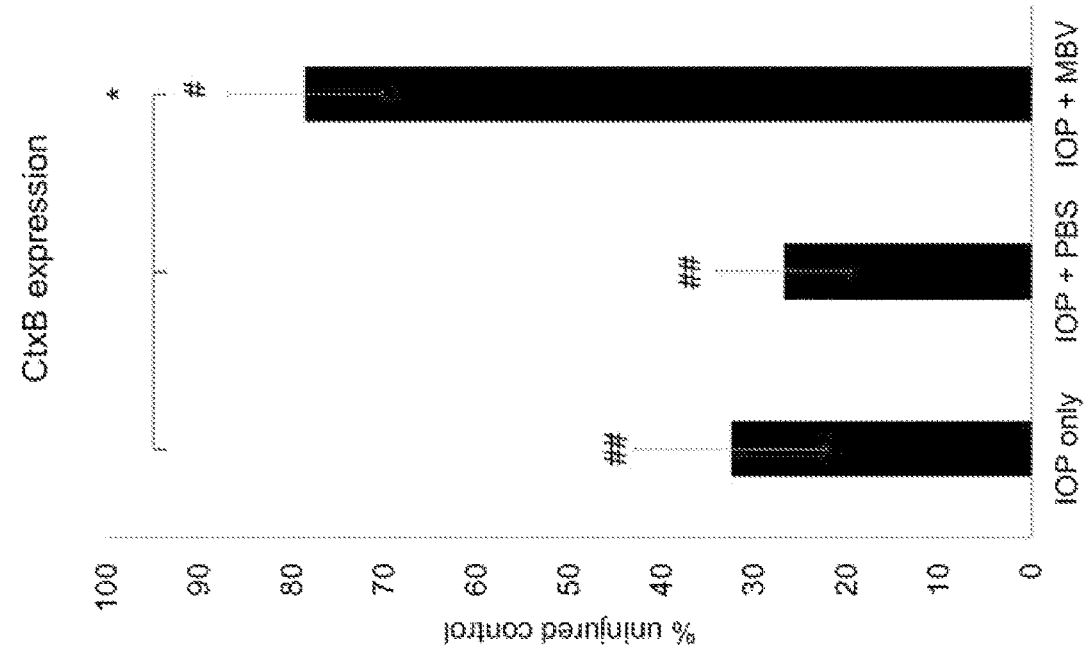
Figure 6B:
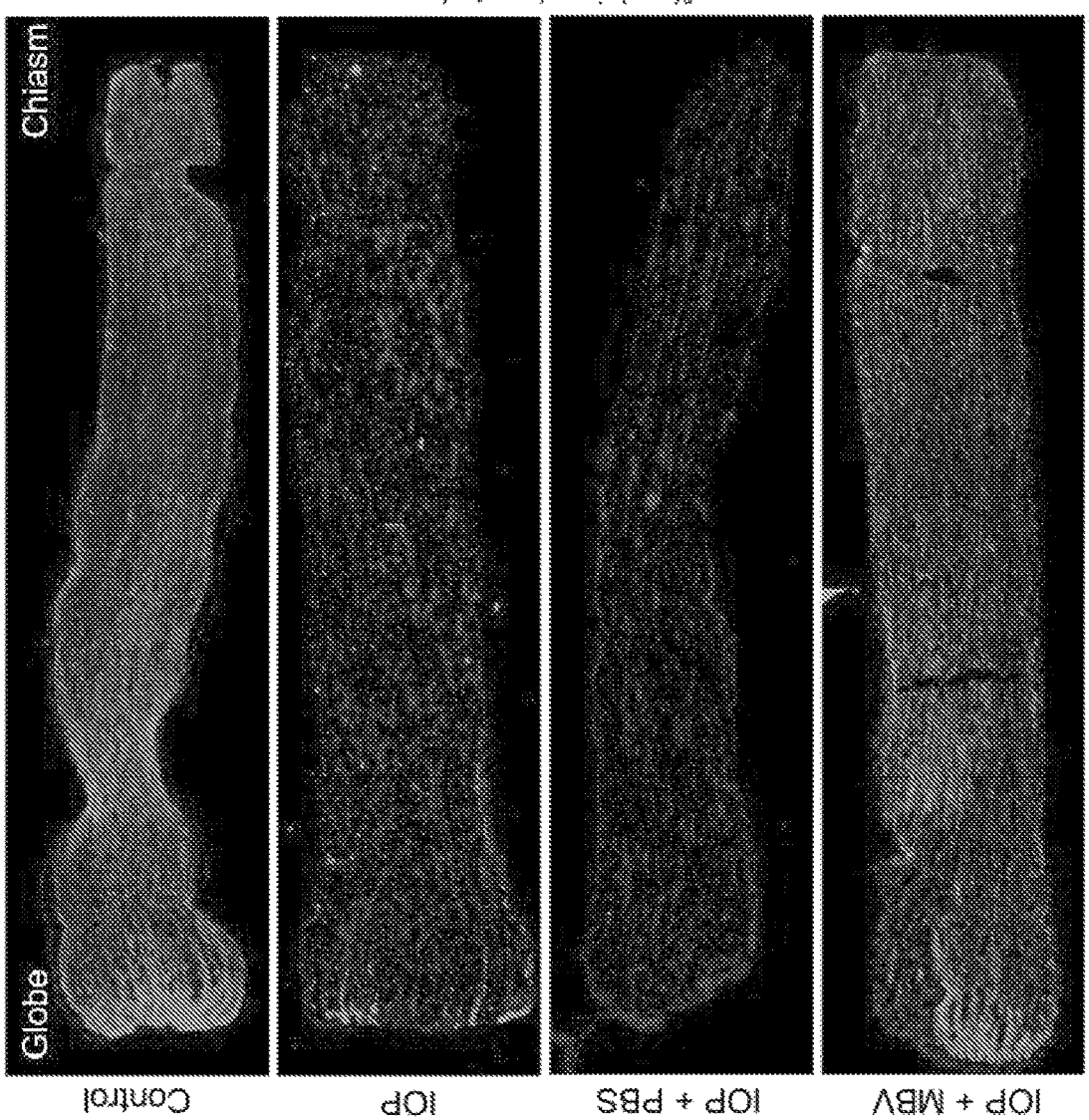

CtxB labeling in the retina showed intact axon labeling in the central and peripheral retina in the healthy control group and decreased axonal labeling in the IOP elevation and IOP elevation with PBS injection groups (FIG. 6A). Animals treated with MBV showed intact axon labeling, similar to healthy control groups, indicating the MBV treatment preserves RGC axons in addition to RGC cell bodies in the retina. In the optic nerves (FIG. 6B), the IOP elevation and IOP elevation with PBS injection groups showed significantly decreased CtxB labeling at 32.5±6.3% and 26.8±4.4% of uninjured control, respectively (FIG. 6C). CtxB labeling in the MBV treated optic nerves was significantly decreased compared to uninjured controls at 78.6±6.1% of controls and was significantly increased compared to both IOP elevation and IOP elevation with PBS injection groups.

Example 8

MBVs Decrease GFAP Expression After IOP Elevation

Figure 7A:
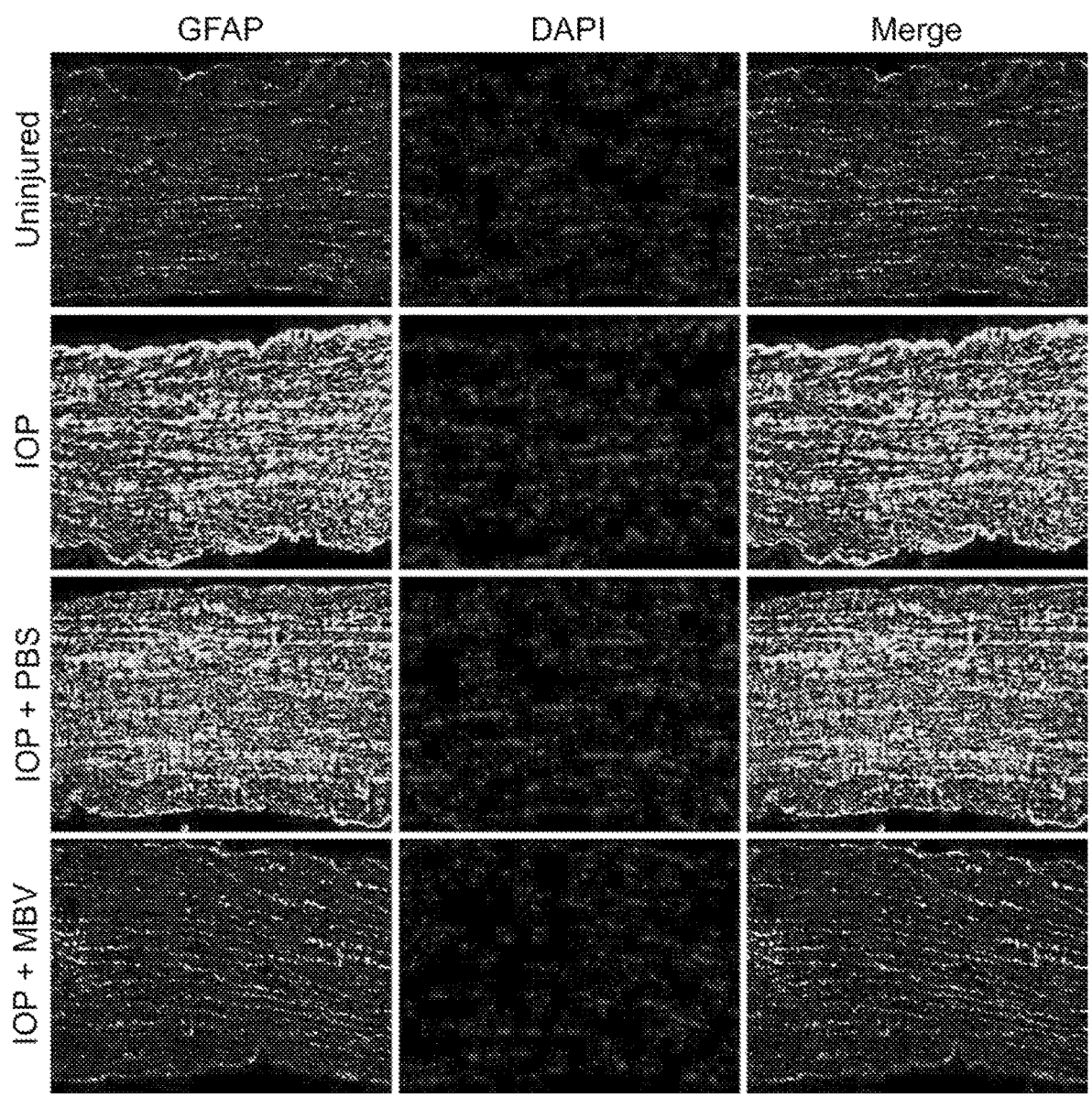

To analyze the effect of MBVs on astrocyte activation in vivo, GFAP expression along the length of the optic nerve was analyzed (FIG. 7A). Compared to uninjured control nerves, GFAP expression significantly increased in the IOP elevation and IOP elevation with PBS injection groups, which is consistent with typical astrocyte migration and activation after optic nerve injury. Quantitatively, IOP elevation and IOP elevation with PBS significantly increased GFAP expression to 393±22.7% and 413.7±26.3%, respectively, compared to uninjured control (FIG. 7B). Qualitatively and quantitatively the optic nerves of animals treated with MBV after IOP elevation showed decreased GFAP expression, and there was no significant difference (107.7±6.4% increase) in GFAP expression between uninjured control optic nerves and MBV treated optic nerves.

Example 9

MBVs Increase GAP43 Expression After IOP Elevation

Figure 8A:
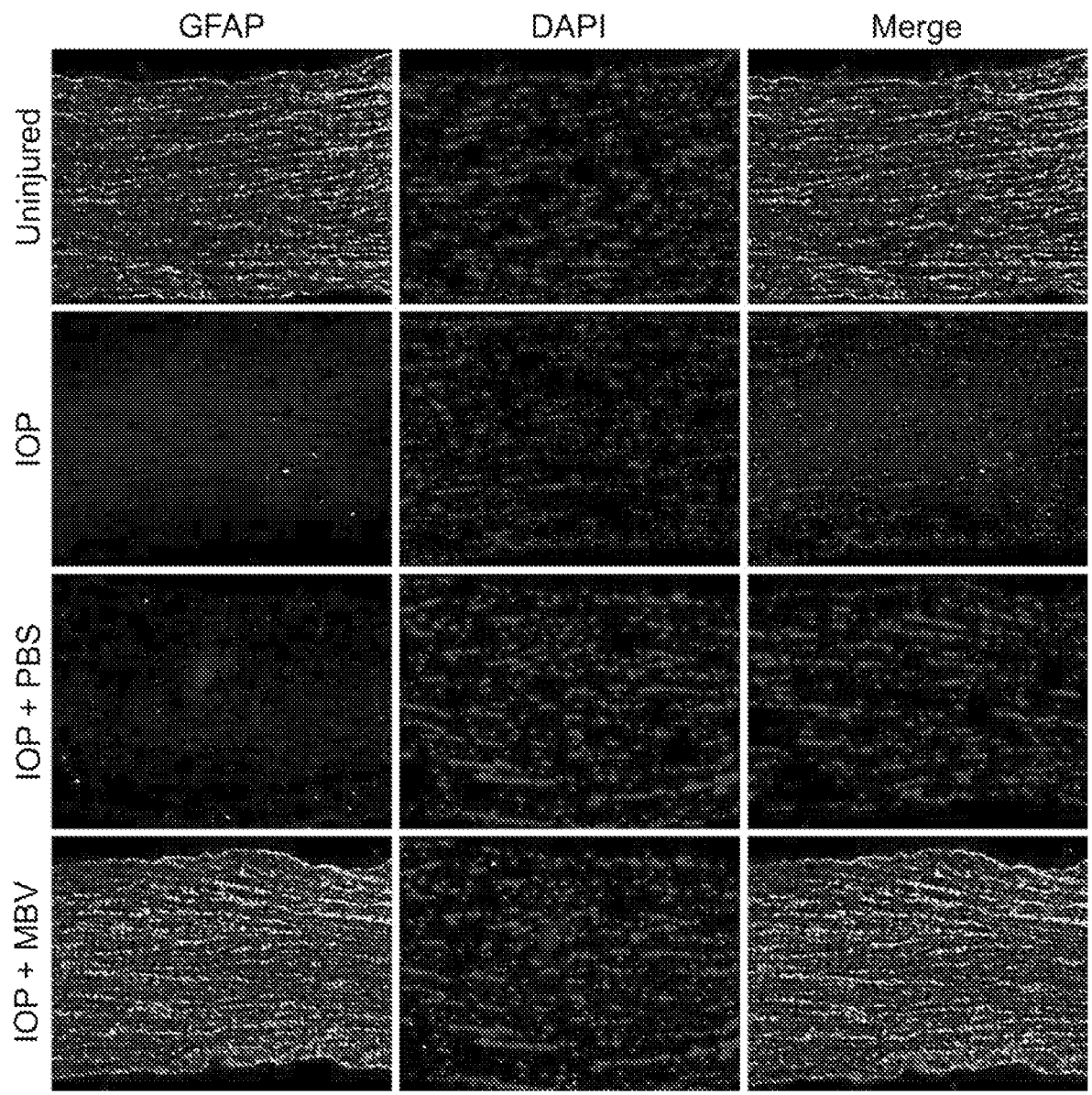
FIGS. 8A-8B. MBV increase GAP-43 expression in the optic nerve. (A) Representative images showing GAP-43 expression in the optic nerve of uninjured control eyes (control), untreated IOP eyes (IOP), PBS treated IOP eyes, and MBV treated IOP eyes. (B) Quantitative analysis of GAP-43 immunoreactivity showed intravitreal MBV injections increase GAP-43 expression in the optic nerve. Error bars represent SEM, experiments represent n=5 animals per groups, 15 images per optic nerve per animal, totaling 75 images analyzed per group. Significance was determined by one-way ANOVA with Post-hoc Tukey's test between groups; #p<0.05, compared to media; *p<0.05 between groups.
Figure 8B:
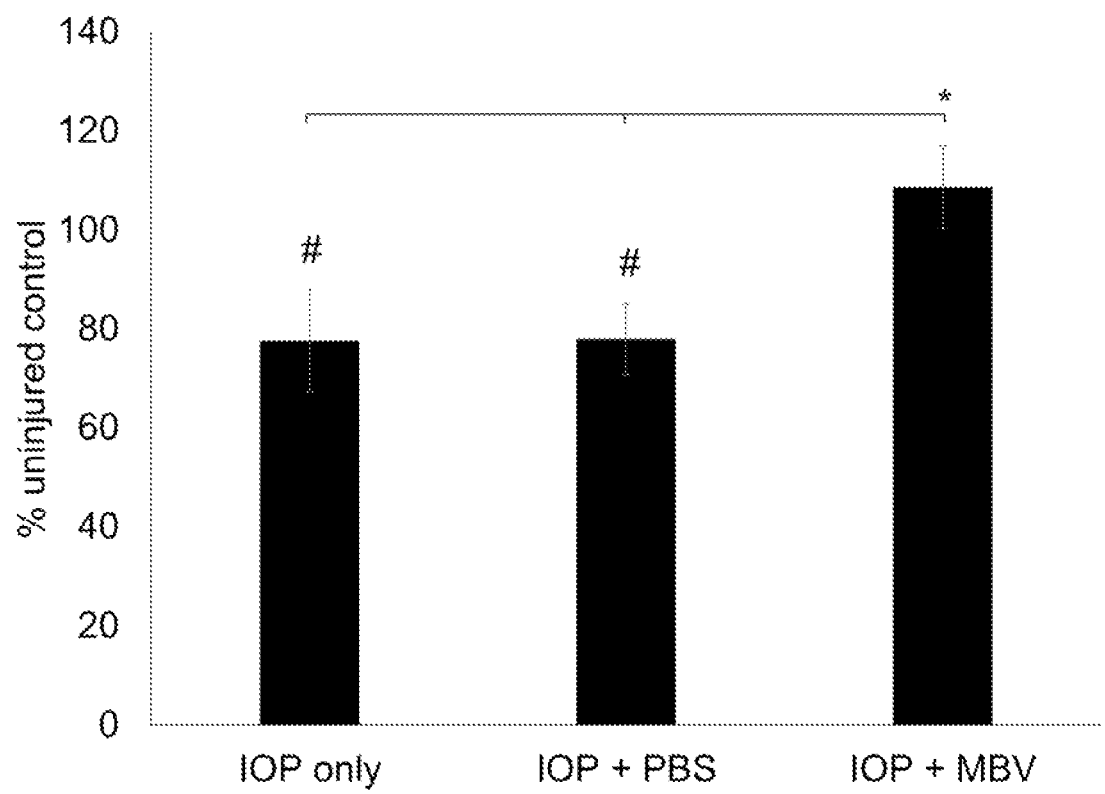

To determine if MBVs can increase RGC axon growth in vivo, the expression of the axon growth marker GAP-43 was analyzed (FIG. 8A). Compared to uninjured control nerves, GAP43 expression was significantly decreased in IOP elevation and IOP elevation with PBS injection groups at 77.5±7.2% and 77.8±8.4% of uninjured controls, respectively (FIG. 8B). Optic nerves of animals treated with MBVs showed increased GAP43 expression, and there was no difference (108.6±6.1%) in GAP43 expression between uninjured control and MBV treated optic nerves.

Example 10

MBVs Improve Retinal Electrical Function After IOP Elevation

Photopic negative response (PhNR) amplitude and latency were recorded using electroretinography (ERG) (FIG. 9). Compared to uninjured control eyes, IOP elevation and IOP elevation with PBS injection significantly decreased PhNR amplitude by 32.8±4.4% and 42.0±16.8%, while there was no difference in PhNR amplitude between uninjured control and MBV treated eyes (FIG. 9C). Latency analysis showed IOP elevation significantly increased latency by 16.6±4.0% compared to uninjured control group, while IOP elevation with PBS injection and MBV treatment had no significant effect on latency (FIG. 9D).

Example 11

MBVs are Distinct from Exosomes

Extracellular vesicles (EV), which include both exosomes and microvesicles), have been shown to be secreted exclusively into the extracellular fluid where they can be relocated freely between cells as well as to distant sites using biological fluids as a mobile liquid medium (FIG. 10). In fact, EVs have been isolated from most types of biological fluids including blood, urine, breast milk, cerebrospinal fluid, and pleural effusions. In addition, EV are secreted into the conditioned media of in-vitro cultured mesenchymal stem cells (MSC). EV isolated from body fluids or from cell culture supernatants are easily identified by the expression of common exosomal surface markers including: CD63, CD81, CD9, and Hsp70.

In contrast to exosomes, Matrix-Bound Nanovesicles (MBV) have recently been reported as an integral and functional component of extracellular matrix (ECM). MBV are a specific subpopulation of vesicle closely associated to collagen fibers within the ECM. It was shown that MBV can be separated from the matrix only after enzymatic digestion of the ECM-scaffold material, suggesting that MBV embedded within ECM are only available for cellular uptake during matrix remodeling events, such as those that occur during normal physiologic processes like wound healing and mechanical stress, or during degradation initiated by the host response to implanted ECM biologic scaffolds (FIG. 10). As a result of their distinct compartmentalization within the matrix, MBV contain a unique set of cell surface markers to allow integration into the matrix. Furthermore, MBV do not express classical surface markers typically associated with exosomes (FIG. 11). Given the differences in their location within the body (i.e. fluid vs ECM-bound), and their differential cargo signature, MBV and exosomes necessarily have differential functions. To demonstrate this, MBV and exosomes were isolated from in-vitro cultured stem cells (FIG. 12). The MBV and exosome samples were then used to stimulate mouse bone-marrow derived macrophages. The results show a distinctive phenotypic profile of macrophages exposed to MBV compared to those stimulated with exosomes (FIG. 13). Importantly, the expression of the pan-macrophage markers F4/80 and CD-11b were significantly reduced in exosome-treated macrophages but not in MBV-treated macrophages. The results demonstrate the differential biologic activities of subpopulations of EV, document that MBV are distinct from exosomes, and demonstrate that MBVs have potential in regenerative medicine. MBVs also contained Lox on their surface.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of increasing retinal ganglion cell survival in a subject in need thereof, comprising:
   selecting a subject in need of increased retinal ganglion cell survival, and
   locally administering to an eye of the subject a therapeutically effective amount of isolated nanovesicles derived from an extracellular matrix, wherein the nanovesicles maintain expression of F4/80 and CD-11b on macrophages in the subject, wherein the nanovesicles comprise lysyl oxidase, and wherein the nanovesicles a) do not express CD63 and CD81, or b) are $CD63^{lo}CD81^{lo}$,
   thereby increasing retinal ganglion cell survival in the subject.

2. The method of claim 1, wherein the extracellular matrix is a mammalian extracellular matrix.

3. The method of claim 2, wherein the mammalian extracellular matrix is a human extracellular matrix.

4. The method of claim 1, wherein the extracellular matrix is derived from esophageal tissue, urinary bladder, small intestinal submucosa, dermis, umbilical cord, pericardium, cardiac tissue, tumor tissue, or skeletal muscle.

5. The method of claim 1, wherein the nanovesicles comprise miR-145 and/or miR-181.

6. The method of claim 1, wherein the nanovesicles are administered intravitreally or subretinally.

7. The method of claim 1, wherein the nanovesicles are administered repeatedly to the eye of the subject.

8. The method of claim 7, wherein the nanovesicles are administered weekly, bimonthly or monthly to the subject.

9. The method of claim 1, wherein the subject has glaucoma.

10. The method of claim 9, further comprising administering to the subject a therapeutically effective amount of an agent that lowers intraocular pressure.

11. The method of claim 10, wherein the agent that lowers intraocular pressure is a) a prostaglandin analog, b) a beta-adrenergic blocker, c) an alpha-adrenergic agonist, or d) a cholinergic agonist.

12. The method of claim 1, wherein the subject has retinal ganglion cell degeneration caused by injury.

13. The method of claim 1, wherein the subject has retinal ganglion cell degeneration caused by a genetic disorder.

14. The method of claim 1, wherein the subject has pressure-independent glaucomatous optic neuropathy, ischemic optic neuropathy, inflammatory optic neuropathy, compressive optic neuropathy, or traumatic optic neuropathy.

15. The method of claim 1, wherein the subject has arteritic ischemic optic neuropathy, arteritic ischemic optic neuropathy associated with giant cell arteritis, nonarteritic ischemic optic neuropathy, infiltrative optic neuropathy, infiltrative optic neuropathy associated with sarcoidosis, infectious optic neuropathy, infectious optic neuropathy associated with syphilis, infectious optic neuropathy associated with Lyme disease, infectious optic neuropathy associated with toxoplasmosis, infectious optic neuropathy associated with herpes zoster, optic neuritis from demyelinating disease, post-radiation optic neuropathy, acrodermatitis enteropathica, hereditary optic neuropathy, hereditary optic neuropathy associated with dominant optic neuropathy, compressive optic neuropathy, compressive optic neuropathy associated with orbital pseudotumor, compressive optic neuropathy associated with thyroid eye disease, autoimmune optic neuropathy, or autoimmune optic neuropathy associated with Lupus.

16. The method of claim 1, wherein the nanovesicles decrease secretion of a cytokine from microglia and/or astrocytes.

17. The method of claim 16, wherein the cytokine is IL-1β, IL-6, or TNF-α.

* * * * *

SEQUENCE LISTING

```
<160> NUMBER OF SEQ ID NOS: 3

<210> SEQ ID NO 1
<211> LENGTH: 88
<212> TYPE: RNA
<213> ORGANISM: Homo sapiens

<400> SEQUENCE: 1
caccuugucc ucacggucca guuuucccag gaaucccuua gaugcuaaga ugggga uucc      60 uggaaauacu guucuugagg ucaugguu                                          88

<210> SEQ ID NO 2
<211> LENGTH: 110
<212> TYPE: RNA
<213> ORGANISM: Homo sapiens
```

```
<400> SEQUENCE: 2
agaagggcua ucaggccagc cuucagagga cuccaaggaa cauucaacgc ugucggugag        60
uuugggauuu gaaaaaacca cugaccguug acuguaccuu gggguccuua                 110

<210> SEQ ID NO 3
<211> LENGTH: 106
<212> TYPE: DNA
<213> ORGANISM: Homo sapiens

<400> SEQUENCE: 3
gcgcagcgcc ctgtctccca gcctgaggtg cagtgctgca tctctggtca gttgggagtc       60
tgagatgaag cactgtagct caggaagaga gaagttgttc tgcagc                     106
```